(12) United States Patent
Tagawa

(10) Patent No.: US 7,030,099 B2
(45) Date of Patent: Apr. 18, 2006

(54) TUMOR SPECIFIC PROMOTERS OF THE MIDKINE GENE THAT ALLOW FOR SELECTIVE EXPRESSION IN P53-INACTIVATED CELLS

(75) Inventor: Masatoshi Tagawa, Chiba (JP)

(73) Assignee: Research Corporation Technologies, Inc., Tucson, AZ (US)

( * ) Notice: Subject to any disclaimer, the term of this patent is extended or adjusted under 35 U.S.C. 154(b) by 23 days.

(21) Appl. No.: 10/333,013

(22) PCT Filed: Jul. 18, 2001

(86) PCT No.: PCT/JP01/06228

§ 371 (c)(1),
(2), (4) Date: Apr. 10, 2003

(87) PCT Pub. No.: WO02/10368

PCT Pub. Date: Feb. 7, 2002

(65) Prior Publication Data

US 2003/0157065 A1  Aug. 21, 2003

(30) Foreign Application Priority Data

Jul. 21, 2000  (JP) .............................. 2000-220504

(51) Int. Cl.
  C07H 21/04 (2006.01)
  A01N 43/04 (2006.01)
  A01N 63/00 (2006.01)
  A01N 65/00 (2006.01)
  A64K 31/70 (2006.01)

(52) U.S. Cl. ..................... 514/44; 514/24.1; 424/93.1; 424/93.2; 536/23.1; 536/24.1; 435/6

(58) Field of Classification Search ................. 514/44; 424/93.1, 93.2; 536/23.1, 24.1; 435/6
See application file for complete search history.

(56) References Cited

U.S. PATENT DOCUMENTS 5,728,379 A * 3/1998 Martuza et al. ............ 424/93.2
6,607,879 B1 * 8/2003 Cocks et al. .................... 435/6

FOREIGN PATENT DOCUMENTS

WO  WO 00/15209 A1  3/2000
WO  WO 00/15242 A1  3/2000

OTHER PUBLICATIONS

Tweddle, et al. (2001) Am. J. Pathol., 158(6): 2067-76.*
Stryer (1988) Biochemistry, 3rd Ed., Freeman and Co., New York, NY., pp. 718, 803-805.*
Levedeva, et al. (2001) Annu. Rev. Pharmacol. Toxicol., 41: 403-19.*
Deonarain (1998) Exp. Opin. Ther. Pat., 8(1): 53-69.*
Gorecki (2001) Exp. Opin. Emerging Drugs, 6(2): 187-98.*
Verma, et al. (1997) Nature, 389: 239-42.*
Eck, et al. (1996) Goodman & Gilman's The Pharmacological Basis of Therapeutics, 9th Ed., McGraw-HIll, New York, NY., pp. 77-101.*
Ausubel, et al. (1995) Short Protocols In Molecular Biology, 3rd Ed., Wiley & Sons, Inc., New York, NY, pp. 3-1 to 3-29.*
Sequence Search Results, Result No. 1, Document labelled "Search 1" (us-10-333-013-copy-539-609.rni).*
Tagawa, et al. (1999) "Preferential expression of a suicide gene in tumor cells is achieved with a promoter of the midkine gene whose expression is up-regulated in a varitey of human tumors", Cancer Gene Therapy, 6(6 Suppl.): S21-S-22, Abstract No. PD-81.*
Adachi, Yasuo, et al., "Midkine Promotor-Based Adenoviral Vector Gene Delivery for Pediatric Solid Tumor", Cancer Research, vol. 60, No. 16, Aug. 15, 2000, pp. 4305-4310.

(Continued)

Primary Examiner—Dave Nguyen
Assistant Examiner—Robert M. Kelly
(74) Attorney, Agent, or Firm—Scully, Scott, Murphy & Presser, P.C.

(57) ABSTRACT

A DNA comprising a 609 bp base sequence from −559 to +50 when the first base sequence of exon 1 of the midkine gene, a human retinoic acid-responsive growth/differentiation factor was set as +1, or a DNA comprising a 251 bp base sequence from −213 to +38 when the transcription initiation point of the c-erbB-2 gene belonging to the EGF receptor family and having a tyrosine kinase activity was set as +1 has a tumor-specific transcription activity, and the promoter activity thereof is high, and therefore is very important as a tumor-specific promoter for use in the suicide gene therapy that combines the use of a gene for a drug metabolizing enzyme and a prodrug for cancer therapy, the gene therapy of cancer using an expression vector that contains a gene encoding a cytokine, and the gene therapy of cancer using an oncolytic virus.

11 Claims, 16 Drawing Sheets

OTHER PUBLICATIONS

Ishii, S. et al., "Charaterization of the Promotor Region of the Human C-ERBB-2 Protooncogene", Proceedings of the National Academy of Sciences of the USA, New York, NY, U.S., vol. 84, No. 13, Jul., 1987, pp. 4374-4378.

Hollywood, D.P., et al., "A Novel Transcription Factor, OB2-1, is Required for Overexpression of the Proto-Oncogene C-ERBB-2 in Mammary Tumour Lines", Embo Journal, Oxford University Press, Surrey, G.B., vol. 12, No. 6, 1993, pp. 2369-2375.

Pandha Hardev, S., et al., "Generic Prodrug Activation Therapy for Breast Cancer: A Phase I Clinical Trial of erbβ-2-directed Suicide Gene Expression", Journal of Clinical Oncology, vol. 17, No. 7, Jul., 1999, pp. 2180-2189.

Grooteclaes, Madeline, et al., "The 6-Kilobase c-erbβ2 Promotor Contains Positive and Negative Regulatory Elements Functional in Human Mammary Cell Lines", Cancer Research, vol. 54, No. 15, 1994, pp. 4193-4199.

M. Miyauchi, et al., "Frequent Expression of Midkine Gene in Esophageal Cancer Sugggests a Potential Usage of Its Promoter for Suicide Gene Therapy", Jpn. Journal of Cancer Research, 1999, vol. 90, No. 4, pp. 469 to 475.

R.C. Pedraza, et al., "A Retinoic Acid-Responsive Element in Human Midkine Gene", J. Biochem., 1995, vol. 117, No. 4, pp. 845 to 849.

K. Uehara, et al., "Genomic Stucture of Human Midkine (MK), a Retinoic Acid-Responsive Growth/Differentiation Factor"., J. Biochem., (1992), vol. 111, No. 5, pp. 563 to 567.

G.K. Scott, et al., "Binding of an ETS-related Protein within the Dnase I Hypersensitive Site of the HER2/neu Promoter in Human Breast Cancer Cells", J. Biol. Chem., 1994, vol. 269, No. 315,pp. 19848 to 19858.

F.L. Moolten., et al., "Drug sensitivity ("suicide") genes for selective ancer chemotherapy", Cancer Gene Ther., (1994). vol. 1, No. 4, pp. 279 to 287.

C. Heise, et al., "Replication-selective adenoviruses as oncolytic agents", J. Clin. Invest., Apr., 2000, vol. 105, No. 7, pp. 847 to 851.

* cited by examiner

CAT ACTIVITY BY MK PROMOTER

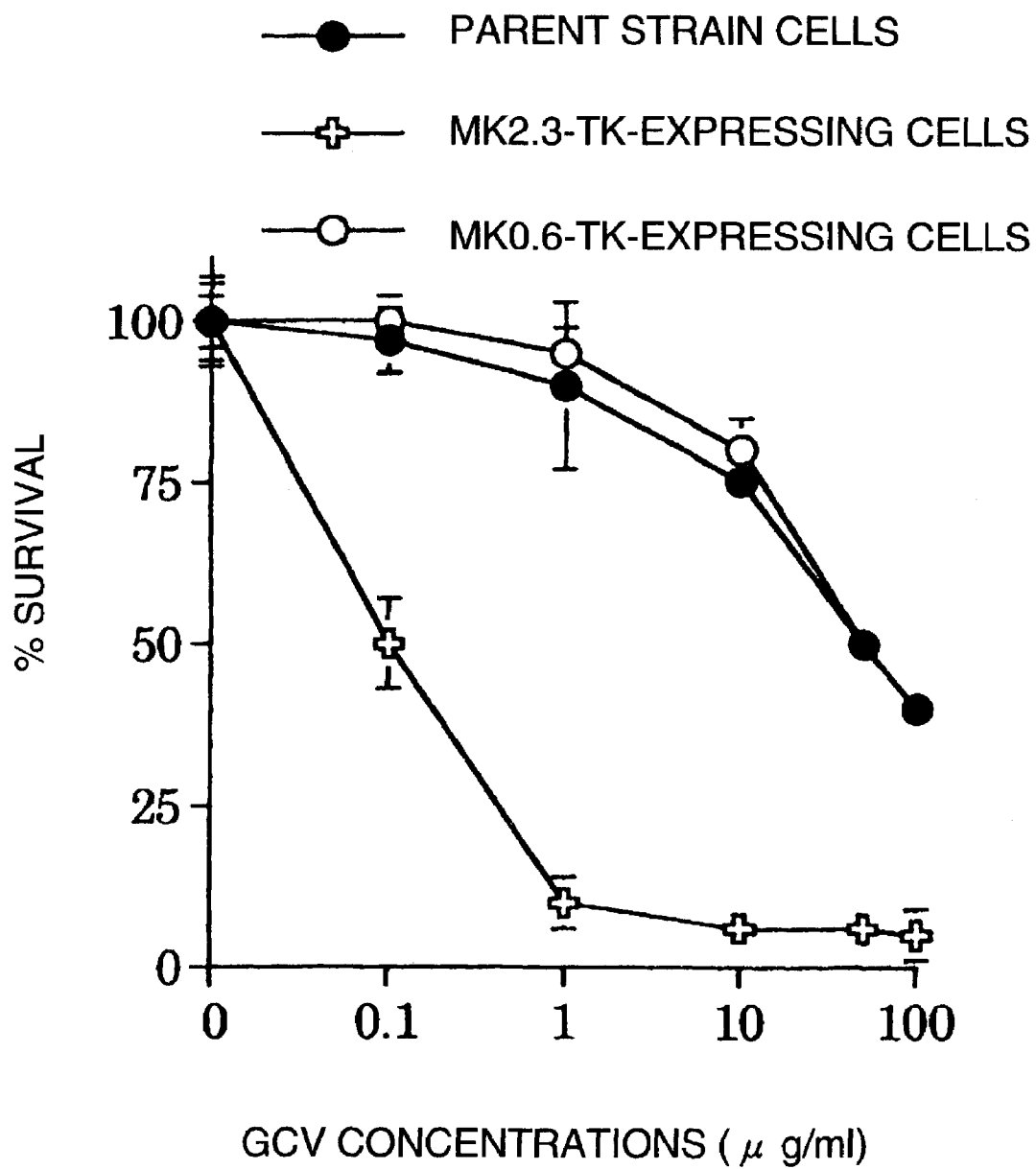

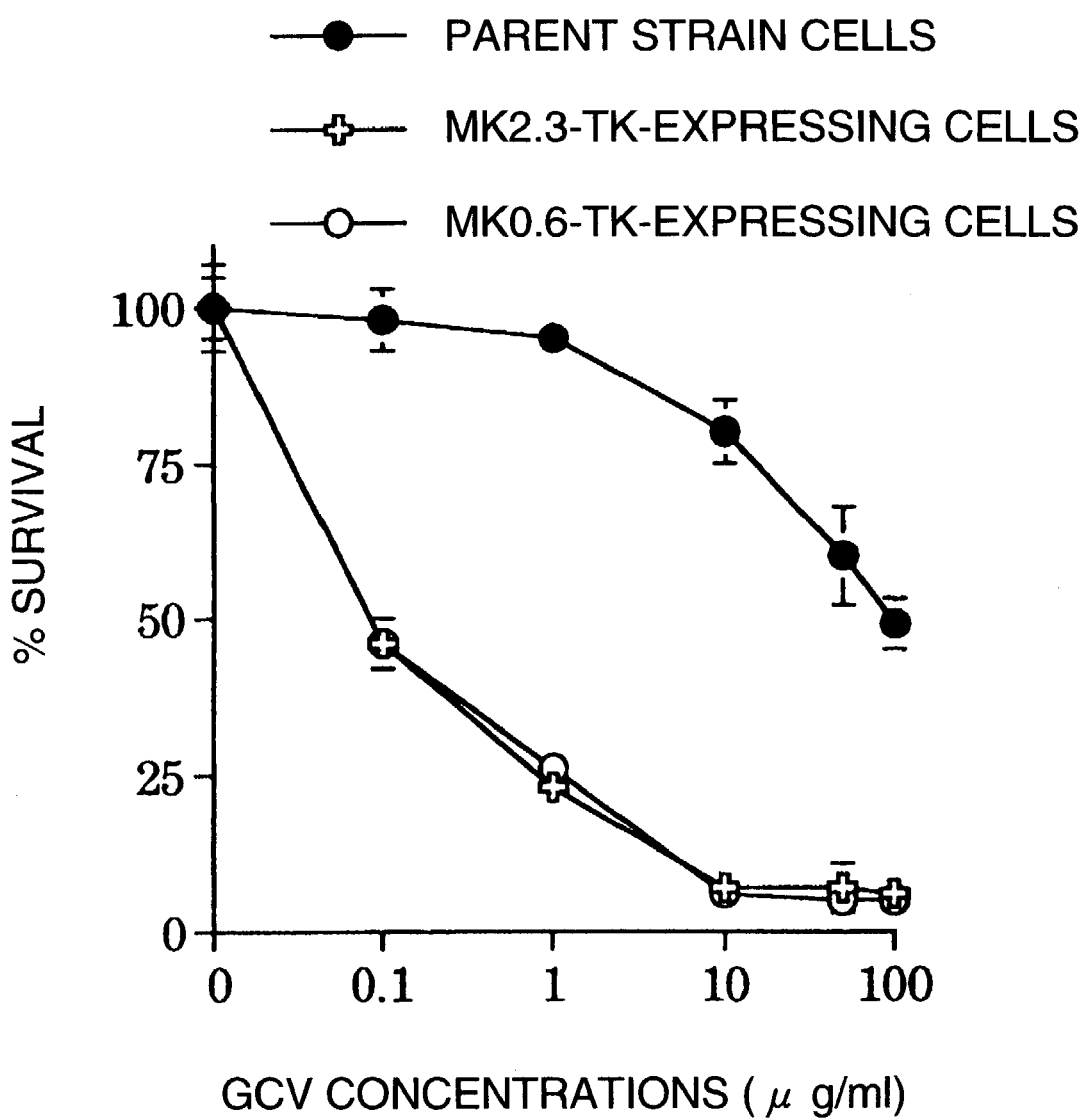

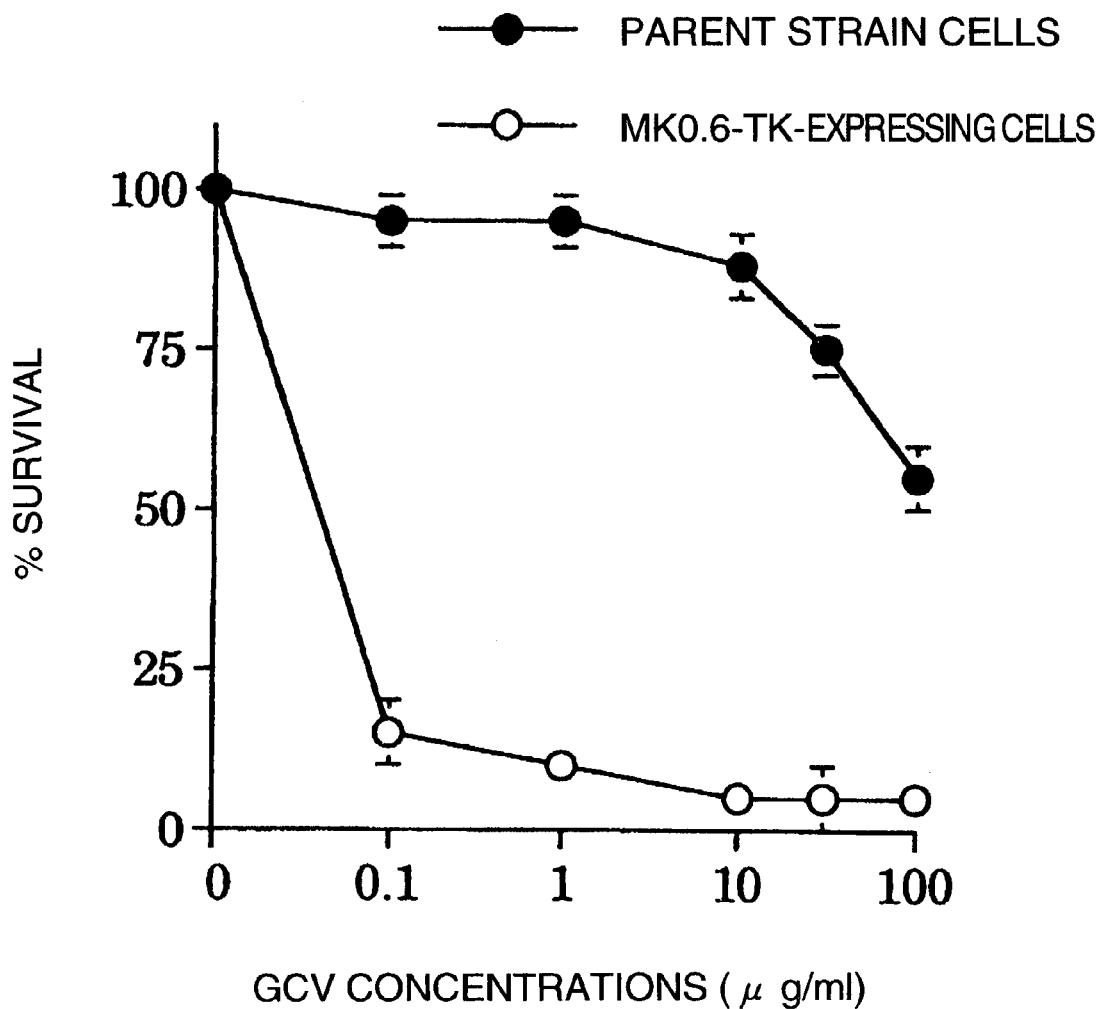

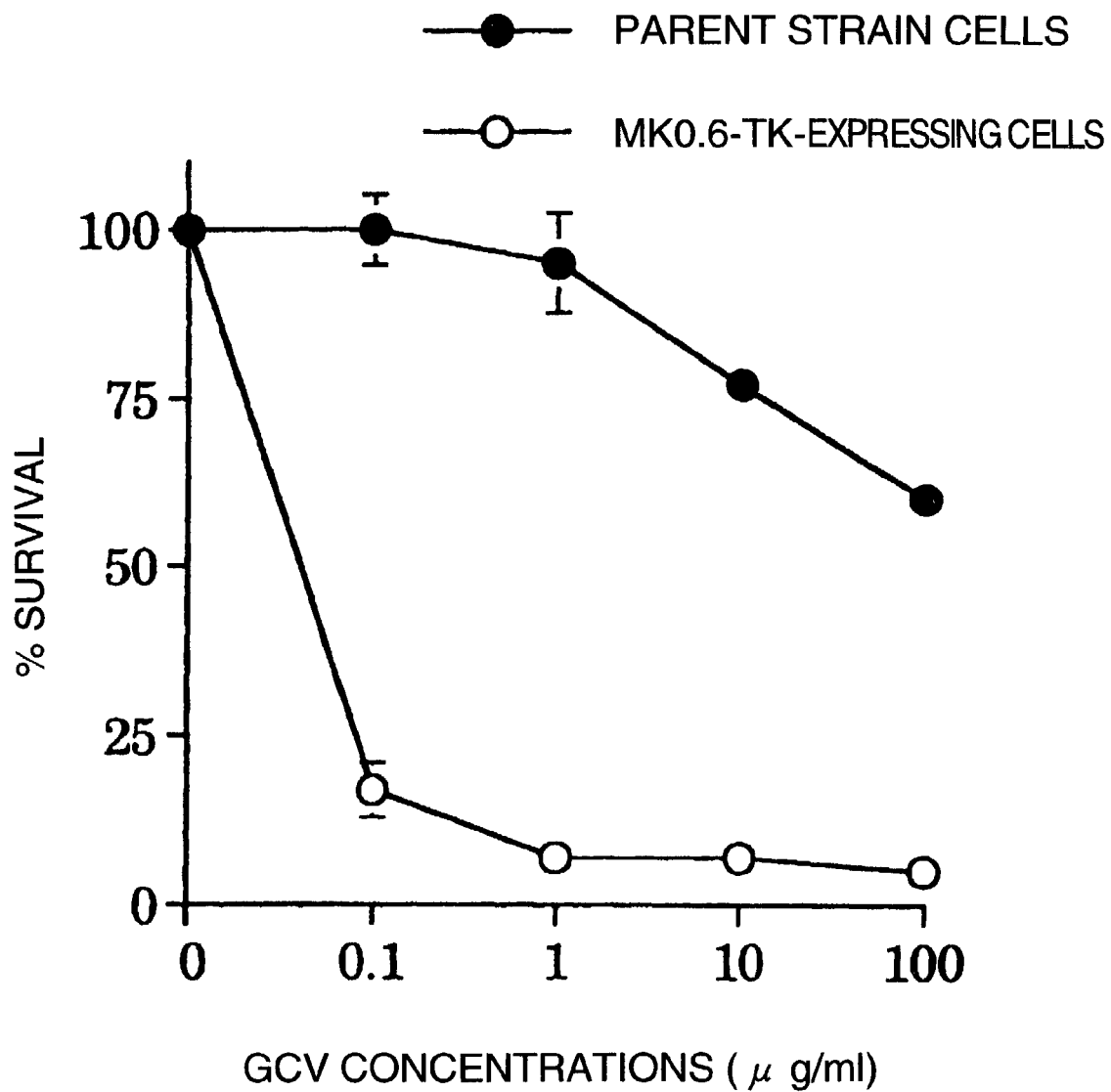

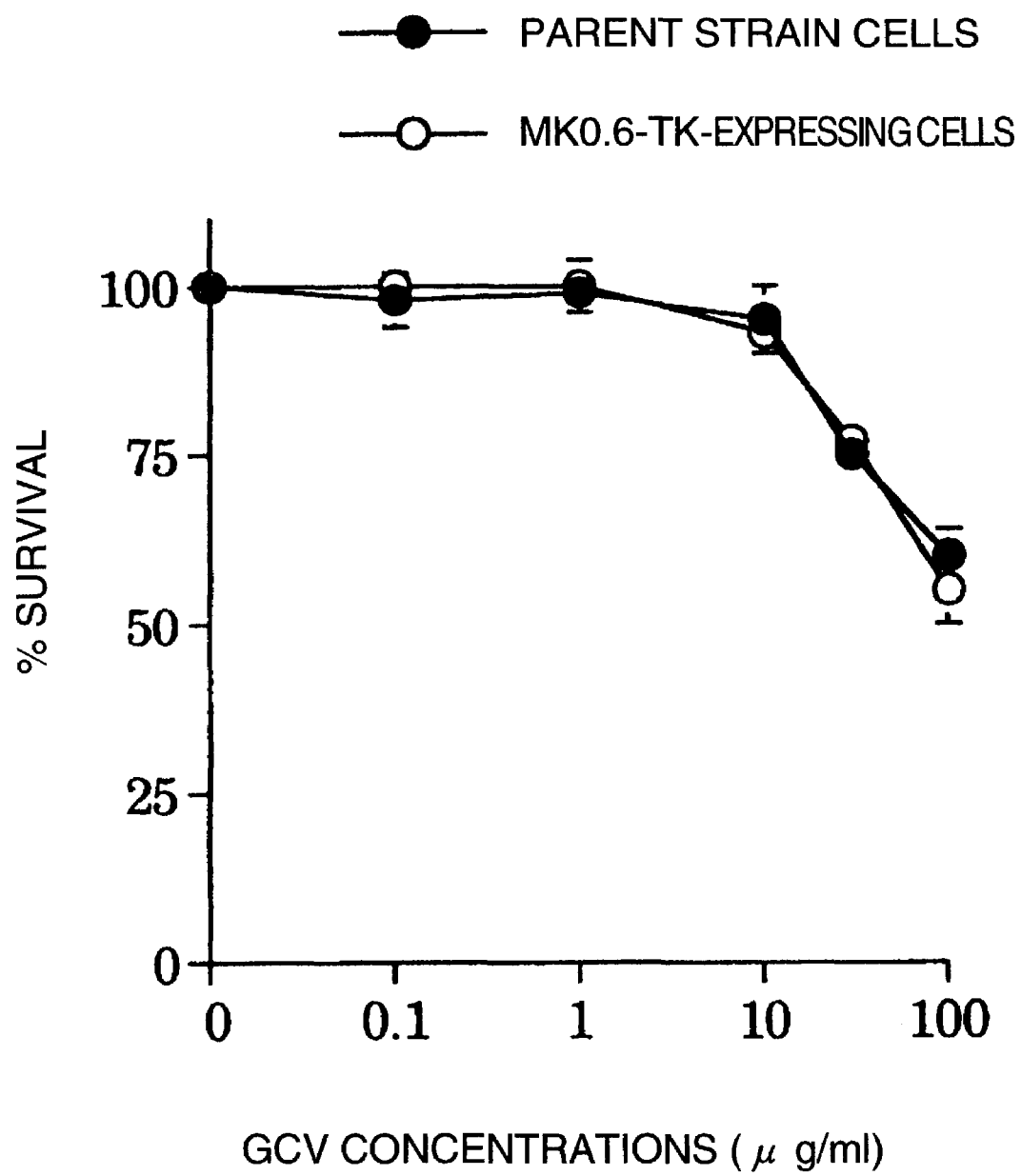

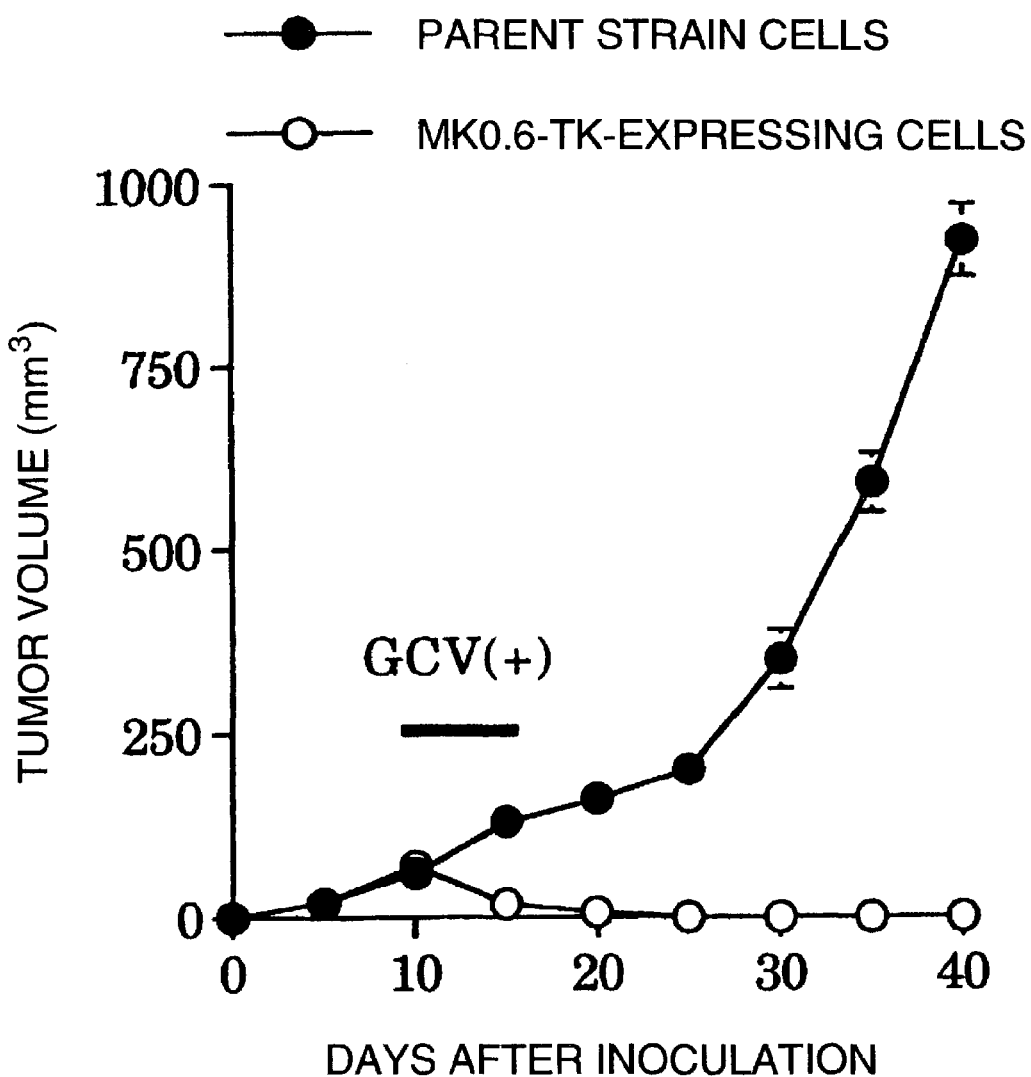

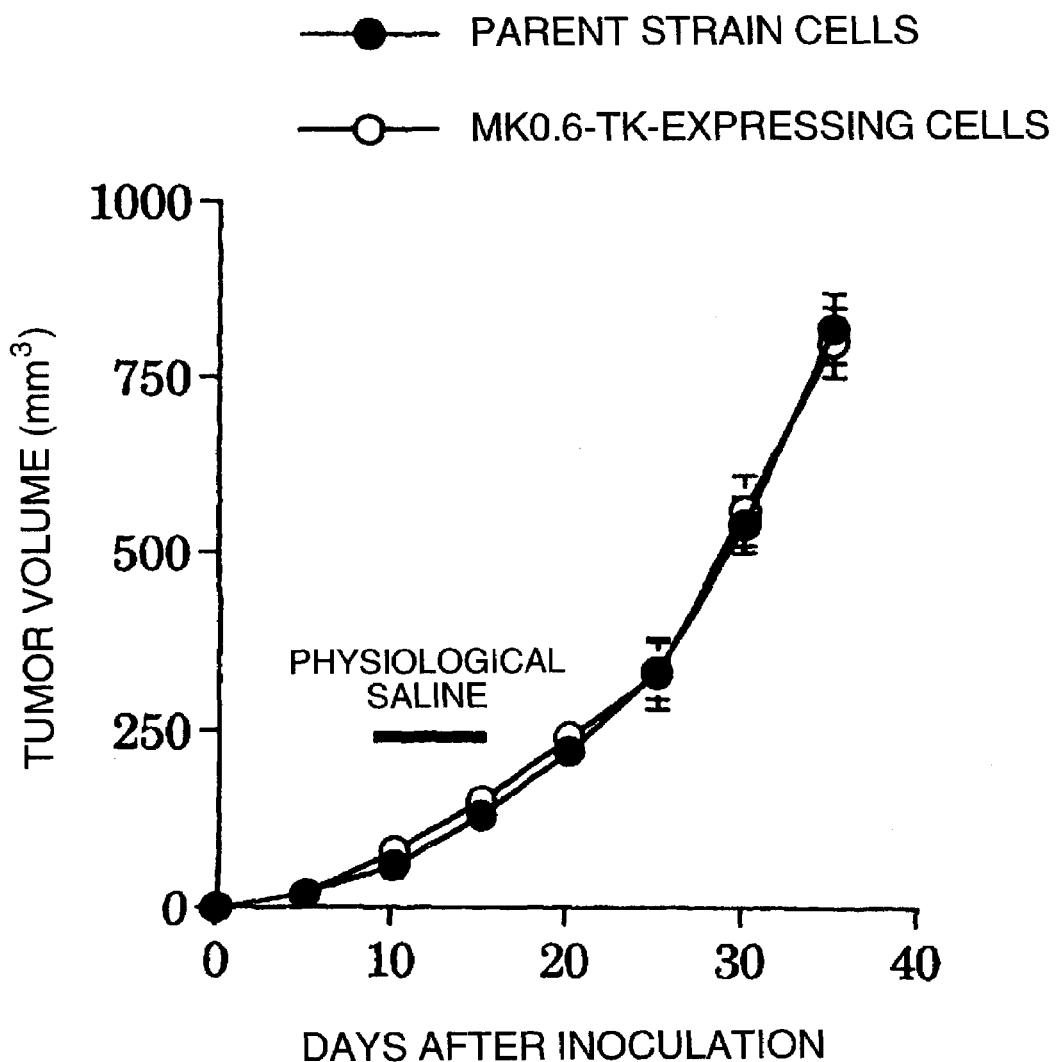

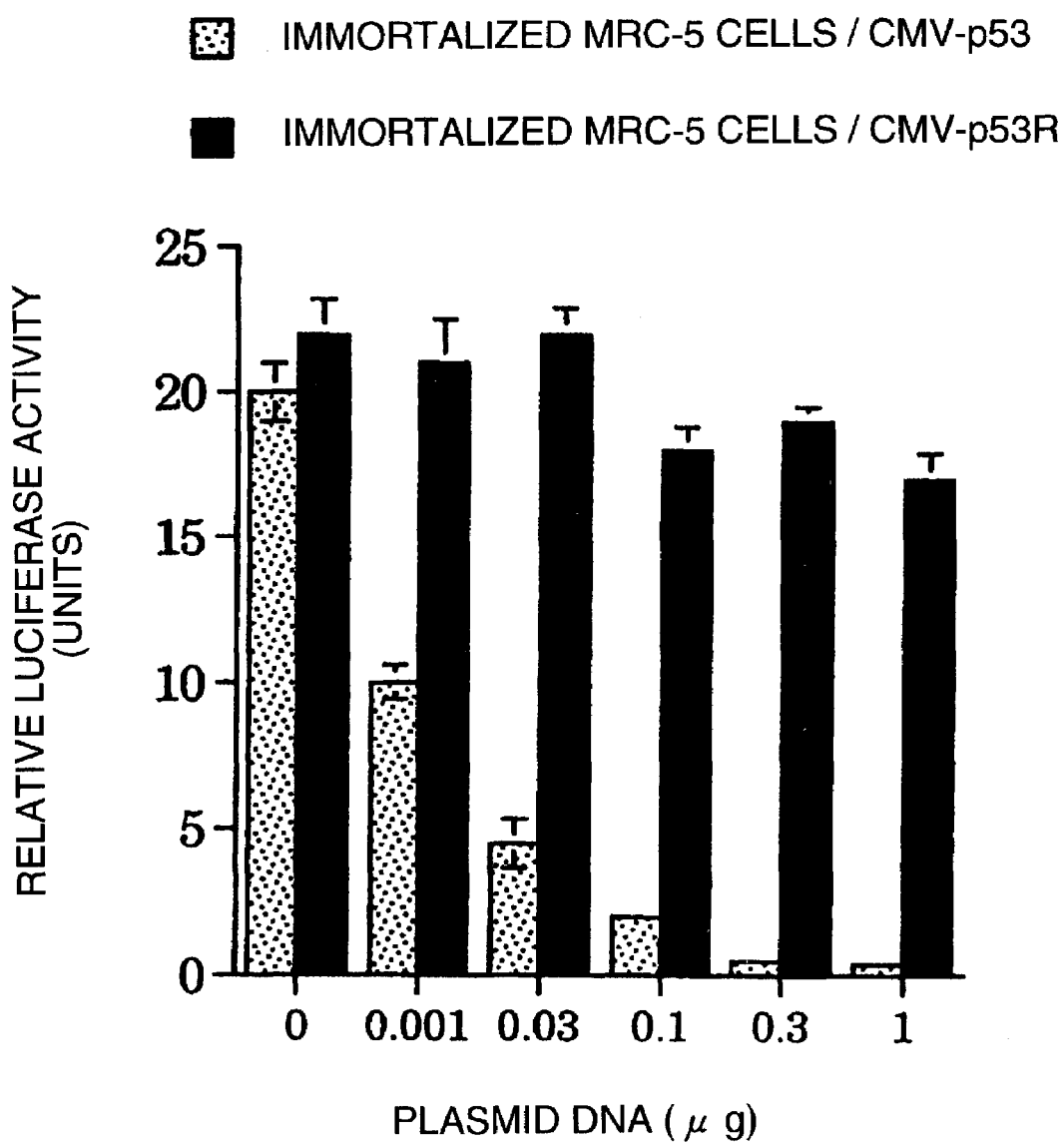

LUCIFERASE ACTIVITY BY MK PROMOTER

LUCIFERASE ACTIVITY BY c-erbB-2 PROMOTER

LUCIFERASE ACTIVITY BY c-erbB-2 PROMOTER

SEQUENCE LISTING

<160> NUMBER OF SEQ ID NOS: 10

<210> SEQ ID NO 1
<211> LENGTH: 609
<212> TYPE: DNA
<213> ORGANISM: Homo sapiens

<400> SEQUENCE: 1

```
gcttccctgc ccacccgcgg aaaccgcccc aggtggccgc gccccctccc cagcagccag      60
cagggcgcca gggctgagcc ggccgtggag gggagcgggt cccgggggtt atacaggcgc     120
cgggcgtccg cggcaggcaa gagaagctga ggcctgagaa cggcccgggc cttggcgtac     180
ggcaggggac gacctgggat gggggcagcg ggcggcggcg cagggagtgg gccggggccg     240
gtgtgcgcgg gcgggacggg gccggggtcg ggagaccacc gctcggaaga tggggccggg     300
```

```
agaggccgcc gtcgcagcgc agagggcacc ggcggggaga cgcgaggacg cggggccggg    360
aacacggacg ccggagtaga agcgcggggg gggcgggctg gagcggggc ggggacgccg    420 gggtcggggg cggtgcgggt ttgagggag ggggcggggc gggtccttcc ctgggggggt    480
ggggagaggg ggcgggggcc catgtgaccg gctcagaccg gttctggaga caaaagggc    540 cgcggcggcc ggagcgggac gggcccggcg cgggagggag cgaagcagcg cgggcagcga    600
gcgagtgag                                                           609

<210> SEQ ID NO 2
<211> LENGTH: 1041
<212> TYPE: DNA
<213> ORGANISM: Homo sapiens

<400> SEQUENCE: 2
ggccgcgctc gtcggggccg ggcgggggcc gatccctccg gcttcccttc ccgcggagaa     60
caacaatgaa agtgaaagag gggtggggcg gggcgagcc cgggttctgt ggcccatttg    120
ccctgtggcc ttgagcaagc ccctccccca ggcctcgggg gctctcccgg tttgggggaa    180
ccgggcgagg caatgccaca ggcccagggt tagaggggt gggcacttgc agctgccgat    240
gtggctggat ctggaacttc tcagacggct cctgtcagcg ccaagtttca ccaaatccag    300
gcctgcgggc tcctcccca ggaccccac tcgcagtccc tcaagcctgt gctcccggaa     360
aggcactggg cgaccgcacc cgtggctttc tctgggcgac cgggtcccag actcccccca    420
gcacagcaga gcgcttccct gcccaccgc ggaaaccgcc ccaggtggcc cgcccctc      480 cccagcagcc agcagggcgc cagggctgag ccggccgtgg aggggagcgg gtcccggggg    540
ttatacaggc gccgggcgtc cgcggcaggc aagagaagct gaggcctgag aacgcccgg    600 gccttggcgt acggcagggg acgacctggg atggggcag cgggcggcgg cgcagggagt     660 gggccgggc cggtgtgcgc gggcgggacg gggccgggt cggagacca ccgctcggaa     720 gatgggccg ggagaggccg ccgtcgcagc gcagagggca ccgcggggga gacgcgagga    780
cgcggggccg ggaacacgga cgccggagta gaagcgcggg gggcgggc tggagcgggg     840 gcggggacgc cggggtcggg ggcggtgcgg gtttgagggg aggggcggg gcgggtcctt    900 ccctgggggg gtggggagag ggggcggggg cccatgtgac cggctcagac cggttctgga    960
gacaaaaggg gccgcggcgg ccggagcggg acgggcccgg cgcgggaggg agcgaagcag   1020
cgcgggcagc gagcgagtga g                                            1041

<210> SEQ ID NO 3
<211> LENGTH: 2335
<212> TYPE: DNA
<213> ORGANISM: Homo sapiens

<400> SEQUENCE: 3
gatcagggga cgggatgggg tacacagcca gcccctgctc ccccagcggg gagacctgtt     60
tgcaccaagc agcggccctg ggccagcgca ccatctgcca ctacatcgtg gaggccgggg    120
cctcgctcat gaagacagac cagcaggtga gcagacggca ggcagggagc ccacgagggc    180
accaaccaaa cctttcccaa ggtcctaggc gggagctggg gctgggggct gtccctggga    240
agacacagtc cagaccctgg gaaacctgag ccagcagggg aggagctggt gggcagagag    300
gcctccctcc ctgaccaggc cacagggagg tagagcccct gcctctcagc ctgctagggg    360
ttaggcctgc ctctggcccc tgctgatcgc agctccgccc tcctcagggg cgacactccc    420
```

-continued

| | |
|---|---|
| cggcagcggg ctgagaaggc tcaggacacc gagctggccg cctacctgga gaaccggcag | 480 |
| cactaccaga tgatccagcg ggaggaccag gagacgcctg tgtagcgggc cgcccacggg | 540 |
| cagcaggagg gacaatgcgg ccaggggacg agcgccttcc ttgcccacct cactgccaca | 600 |
| ttccagtggg acgccacgg ggggacctag gccccaggga aagagcccca tgccgccccc | 660 |
| taaggagccg cccagaccta gggctggact caggagctgg gggggcctca cctgttcccc | 720 |
| tgaggacccc gccggacccg gaggctcaca gggaacaaga cacggctggg ttggatatgc | 780 |
| ctttgccggg gttctggggc agggcgctcc ctggccgcag cagatgccct cccaggagtg | 840 |
| ggaggggctg gagaggggga ggccttcggg aagaggcttc ctgggccccc tggtcttcgg | 900 |
| ccgggtcccc agccccgct cctgccccac cccacctcct ccgggcttcc tcccggaaac | 960 |
| tcagcgcctg ctgcacttgc ctgccctgcc ttgcttggca cccgctccgg cgaccctccc | 1020 |
| cgctcccctg tcatttcatc gcggactgtg cggcctgggg gtgggggggcg ggactctcac | 1080 |
| ggtgacatgt ttacagctgg gtgtgactca gtaaagtgga tttttttttc ttttctgctt | 1140 |
| ttcttctttt gcgggggagg tctaacaacc agcgggggct gcggggttgt cctcggggtg | 1200 |
| ggggactgga cgctgtcgac agcaccttcc tggggccccg gctcccgttt ggtggttggt | 1260 |
| cccagggcct gcccggttcc tgacctctgc ccgcggccgc gctcgtcggg gccgggcggg | 1320 |
| ggccgatccc tccggcttcc cttcccgcgg agaacaacaa tgaaagtgaa agaggggtgg | 1380 |
| ggcgggggcg agcccgggtt ctgtggccca tttgccctgt ggccttgagc aagcccctcc | 1440 |
| cccaggcctc gggggctctc ccggtttggg ggaaccgggc gaggcaatgc cacaggccca | 1500 |
| gggttagagg gggtgggcac ttgcagctgc cgatgtggct ggatctggaa cttctcagac | 1560 |
| ggctcctgtc agcgccaagt ttcaccaaat ccaggcctgc gggctcctcc cccaggaccc | 1620 |
| ccactcgcag tccctcaagc ctgtgctccc ggaaaggcac tgggcgaccg cacccgtggc | 1680 |
| tttctctggg cgaccgggtc ccagactccc cccagcacag cagagcgctt ccctgcccac | 1740 |
| ccgcggaaac cgccccaggt ggccgcgccc cctccccagc agccagcagg gcgccagggc | 1800 |
| tgagccggcc gtggagggga gcgggtcccg ggggttatac aggcgccggg cgtccgcggc | 1860 |
| aggcaagaga agctgaggcc tgagaacggc ccgggccttg gcgtacggca ggggacgacc | 1920 |
| tgggatgggg gcagcgggcg gcggcgcagg gagtgggccg gggccggtgt gcgcgggcgg | 1980 |
| gacgggccg gggtcgggag accaccgctc ggaagatggg gccgggagag gccgccgtcg | 2040 |
| cagcgcagag ggcaccggcg gggagacgcg aggacgcggg gccgggaaca cggacgccgg | 2100 |
| agtagaagcg cggggggggc gggctggagc ggggggcggg acgccgggt cggggcggt | 2160 |
| gcgggtttga ggggagggg cggggcgggt ccttccctgg ggggtgggg agaggggcg | 2220 |
| ggggcccatg tgaccggctc agaccggttc tggagacaaa aggggccgcg gcggccggag | 2280 |
| cgggacgggc ccggcgcggg agggagcgaa gcagcgcggg cagcgagcga gtgag | 2335 |

<210> SEQ ID NO 4
<211> LENGTH: 335
<212> TYPE: DNA
<213> ORGANISM: Homo sapiens

<400> SEQUENCE: 4

| | |
|---|---|
| accaccgctc ggaagatggg gccgggagag gccgccgtcg cagcgcagag ggcaccggcg | 60 |
| gggagacgcg aggacgcggg gccgggaaca cggacgccgg agtagaagcg cggggggggc | 120 |
| gggctggagc ggggggcggg acgccgggt cggggcggt gcgggtttga ggggagggg | 180 |
| cggggcgggt ccttccctgg ggggtgggg agaggggcg ggggcccatg tgaccggctc | 240 |

```
agaccggttc tggagacaaa aggggccgcg gcggccggag cgggacgggc ccggcgcggg    300
agggagcgaa gcagcgcggg cagcgagcga gtgag                              335
```

<210> SEQ ID NO 5
<211> LENGTH: 194
<212> TYPE: DNA
<213> ORGANISM: Homo sapiens

<400> SEQUENCE: 5

```
cgccggggtc gggggcggtg cgggtttgag gggaggggc ggggcgggtc cttccctggg    60
ggggtgggga gaggggggcgg gggcccatgt gaccggctca gaccggttct ggagacaaaa   120
ggggccgcgg cggccggagc gggacgggcc cggcgcggga gggagcgaag cagcgcgggc   180
agcgagcgag tgag                                                    194
```

<210> SEQ ID NO 6
<211> LENGTH: 70
<212> TYPE: DNA
<213> ORGANISM: Homo sapiens

<400> SEQUENCE: 6

```
ccgcggcggc cggagcggga cgggcccggc gcgggaggga gcgaagcagc gcggcagcg    60 agcgagtgag                                                         70
```

<210> SEQ ID NO 7
<211> LENGTH: 533
<212> TYPE: DNA
<213> ORGANISM: Homo sapiens

<400> SEQUENCE: 7

```
gggggtcctg gaagccacaa ggtaaacaca acacatcccc ctccttgact atcaatttta   60
ctagaggatg tggtgggaaa accattattt gatattaaaa caaataggct tgggatggag   120
taggatgcaa gctccccagg aaagtttaag ataaaacctg agacttaaaa gggtgttaag   180
agtggcagcc tagggaattt atcccggact ccggggggagg gggcagagtc accagcctct   240
gcatttaggg attctccgag gaaaagtgtg agaacggctg caggcaaccc aggcgtcccg   300
gcgctaggag ggacgaccca ggcctgcgcg aagagaggga gaaagtgaag ctgggagttg   360
ccgactccca gacttcgttg gaatgcagtt ggagggggcg agctgggagc gcgcttgctc   420
ccaatcacag gagaaggagg aggtggagga ggagggctgc ttgaggaagt ataagaatga   480
agttgtgaag ctgagattcc cctccattgg gaccggagaa accaggggag ccc          533
```

<210> SEQ ID NO 8
<211> LENGTH: 344
<212> TYPE: DNA
<213> ORGANISM: Homo sapiens

<400> SEQUENCE: 8

```
ctagggaatt tatcccggac tccggggggag ggggcagagt caccagcctc tgcatttagg   60
gattctccga ggaaaagtgt gagaacggct gcaggcaacc caggcgtccc ggcgctagga   120
gggacgaccc aggcctgcgc gaagagaggg agaaagtgaa gctgggagtt gccgactccc   180
agacttcgtt ggaatgcagt tggagggggc gagctgggag cgcgcttgct cccaatcaca   240
ggagaaggag gaggtggagg aggagggctg cttgaggaag tataagaatg aagttgtgaa    300
gctgagattc ccctccattg ggaccggaga accagggga gccc                      344
```

```
<210> SEQ ID NO 9
<211> LENGTH: 251
<212> TYPE: DNA
<213> ORGANISM: Homo sapiens

<400> SEQUENCE: 9
ggcaacccag gcgtcccggc gctaggaggg acgacccagg cctgcgcgaa gagagggaga      60
aagtgaagct gggagttgcc gactcccaga cttcgttgga atgcagttgg aggggggcgag    120 ctgggagcgc gcttgctccc aatcacagga gaaggaggag gtggaggagg agggctgctt    180
gaggaagtat aagaatgaag ttgtgaagct gagattcccc tccattggga ccggagaaac    240
caggggagcc c                                                           251

<210> SEQ ID NO 10
<211> LENGTH: 124
<212> TYPE: DNA
<213> ORGANISM: Homo sapiens

<400> SEQUENCE: 10
cgcgcttgct cccaatcaca ggagaaggag gaggtggagg aggagggctg cttgaggaag      60
tataagaatg aagttgtgaa gctgagattc ccctccattg ggaccggaga aaccagggga    120
gccc                                                                   124
```

TUMOR SPECIFIC PROMOTERS OF THE MIDKINE GENE THAT ALLOW FOR SELECTIVE EXPRESSION IN P53-INACTIVATED CELLS

TECHNICAL FIELD

The present invention relates to a tumor-specific promoter that permits the expression of foreign genes in tumor cells or tumor tissues in a tumor-specific manner. More specifically, it relates to a tumor-specific promoter that enables a high transcriptional activity in tumor cells or tumor tissues in a tumor-specific manner, and that can be widely used in gene therapy of cancer, for example, suicide gene therapy comprising a gene encoding a drug metabolizing enzyme and a prodrug for cancer therapy, immune gene therapy that treats cancer by introducing cytokine genes into cancer cells and thus by enhancing the body's immunological functions and gene therapy of cancer using an oncolytic virus that kills only tumor cells, and the like.

BACKGROUND ART

With regard to cancer therapy, in recent years, much attention has been paid to gene therapy of cancer wherein a foreign gene is introduced into the cell to treat cancer. Gene therapy of cancer includes: the gene therapy that targets oncogenes and/or tumor suppressor genes wherein the action of oncogenes is suppressed or the denatured tumor suppressor genes are reactivated; the suicide gene therapy wherein a gene for drug metabolizing enzyme that is not originally present in human cells is introduced into tumor cells and then a prodrug for cancer therapy that is activated by the said enzyme is administered so as to kill only the cells into which the gene for a drug metabolizing enzyme has been introduced; the immunological gene therapy wherein cytokine genes are etc. introduced into the cell so as to enhance the immunological functions inherent to human and thereby to treat cancer; a gene therapy wherein a tumor-specific promoter is inserted upstream of adenovirus E1A or E1B gene that is one of the early genes and is essential for the propagation of adenoviruses so as to construct an oncolytic virus that specifically propagates in the integrated tumor cells, and tumor cells are specifically killed by this virus, and the like.

In such gene therapies, specific expression of the desired gene in tumor cells or tumor tissues has an important meaning from the viewpoint of efficiency and safety of gene therapy, and is one of the challenges encountered by gene therapy today. In order to permit such tumor-specific gene expression, it is important to develop a promoter that regulates the expression of the introduced gene in a tumor-specific manner.

As tumor-specific promoters, there are known α-fetoprotein promoter, carcinoembryonic antigen (CEA) promoter, prostate specific antigen promoter and the like. However, these promoters lack flexibility since the scope in which they can be applied is limited and the promoter activity is not high. Thus, the gene therapy using these promoters has a very limited scope of application.

On the other hand, a new retinoic acid-responsive growth/differentiation factor, midkine, a heparin-binding protein, was discovered from teratoma cells, and the gene thereof has been cloned (Kodomatsu, K. et al., Biochem. Biophys. Res. Commun. 151:1312–1318, 1988). Though the biological functions of the protein have not been fully elucidated, its expression frequency and expression level are high in many kinds of human gastrointestinal cancers (colon cancer, pancreatic cancer, hepatic cancer etc.), lung cancer, breast cancer, neuroblastoma, brain tumor etc. (Tsutui, J. et al., Cancer Res., 53:1281–1285, 1993; Aridome, K. et al., Jpn. J. Cancer Res., 86:655–661, 1995; Muramatsu, H. et al., J. Biochem., 119:1171–1175, 1996; O'Brien, T. et al., Cancer Res., 56:2515–2518, 1996).

c-erbB-2 (HER2/neu) belongs to the EGF receptor family and has a tyrosine kinase activity. Although this gene is expressed slightly in the normal epithelial cells, it is highly expressed in breast cancer and other cancers such as esophageal cancer, gastric cancer and ovarian cancer (Slamon, D J et al., Science, 244:707–712, 1989; Hynes, N E et al., Biochim. Biophys. Acta, 1198:165–184, 1994). Furthermore, it has been reported that its high expression in breast cancer is associated with resistance to anti-cancer agents and is thereby a factor responsible for poor prognosis (Hynes, N E et al., Biochim. Biophys. Acta, 1198:165–184, 1994).

The promoter regions of the midkine gene and the c-erbB-2 gene are also being extensively studied.

Thus, it has been demonstrated that 2.3 kb in the 5'-end upstream region of the midkine gene can be used as a promoter that induces the transcription activity of the gene in the tumor cells and that it can be used as a promoter for the suicide gene therapy in which the herpes simplex virus-thymidine kinase (HSV-TK), a drug-metabolizing enzyme gene, and gancyclovir, a prodrug for cancer therapy, were combined (Miyauchi, M. et al., Jpn. J. Cancer Res., 90:469–475, 1999; Adachi, Y. et al., Mol. Ther., 1: S238, 2000). However, the tumor-specificity and the promoter activity of the 2.3 kb at the 5'-end upstream region of the midkine gene is not fully high.

Although the promoter region of the c-erbB-2 gene has also been analyzed, previous studies used animal species other than humans and tumor cells other than breast cancer and thus the identification of the minimal promoter region differed with different reports (Ishii, S. et al., Proc. Natl. Acad. Sci. USA, 84:4374–4378, 1987; Hudson, L G et al., J. Biol. Chem., 265:4389–4393, 1990; Hollywood, D P et al., EMBO J., 12:2369–2375, 1993; Scott, G K et al., J. Biol. Chem., 269:19848–19858, 1994; Benz, C C et al., Oncogene, 15:1513–1525, 1997; Grooteclaes, M. et al., Cancer Res., 59:2527–2531, 1999). However, there are many reports which described that, when the base at position 1259 of the c-erbB-2 promoter gene (Accession No. J05264) registered at the NCBI GeneBank is set as the transcription initiation point +1, a promoter activity was mapped in the −700 bp (−662/+38) region or the −533 bp (−435/+38) region, and it has been recognized that the activity lies approximately in this range. There are also reports which described that a promoter activity lied in −213/+38 or −87/+38 region, but their tumor specificity has not been studied and that the general promoter region of the c-erbB-2 gene but not tumor-specific regions has merely been examined using tumor cells. In fact, all of the previous reports that used the c-erbB-2 promoter for the expression of suicide genes have used the 533 bp (−465/+38) or longer regions containing the 533 bp (Harris, J D et al., Gene Ther., 1:170–175, 1994; Ring, C J A et al., Gene Ther., 3:1094–1103, 1996; Takakuwa, K. et al., Jpn. J. Cancer Res., 88:166–175, 1997; Pandha, H S et al., J. Clin. Oncol., 17:2180–2189, 1999). Furthermore, there is also a report that the 257 bp (−256/+1) region of the c-erbB-2 gene has a promoter activity specific to cancer (Japan Society of Gene Therapy, Abstract, issued on Jul. 18, 1999, page 98; Japan Society of Gene Therapy, Abstract, issued on Jul. 28, 2000, page 65). However, this region does not have fully high tumor-specificity or high promoter activity, either.

Thus, there has been a need for the development of tumor-specific promoters that have fully high tumor-specificity and high promoter activity, and that can be effectively used in gene therapy.

DISCLOSURE OF INVENTION

After intensive and extensive research in order to obtain tumor-specific promoters that have fully high tumor-specificity and promoter activity, the present inventor has found that by using specific partial sequences within the 2.3 kb localized in the 5'-end upstream region of the midkine gene as a promoter or by using specific partials sequence in the regulatory regions of the c-erbB-2 gene as a promoter, a tumor-specific promoter having a fully high tumor-specificity and promoter activity can be obtained, and that it can be effectively used for gene therapy, and thereby have completed the present invention.

Thus, the present invention is a tumor-specific promoter that has a base sequence starting from any base at positions 1–539 to a base at position 609 in the base sequence set forth in SEQ ID NO: 1 of the sequence listing, or a base sequence from starting any base at positions 1–127 to a base at position 251 in the base sequence set forth in SEQ ID NO: 9.

Furthermore, the present invention is a tumor-specific promoter that hybridizes under a stringent condition to a base sequence starting from any base at positions 1–539 to a base at position 609 in the base sequence set forth in SEQ ID NO: 1 of the sequence listing, or a base sequence starting from any base at positions 1–127 to a base at position 251 in the base sequence set forth in SEQ ID NO: 9, and that has a promoter function similar to those base sequences.

Furthermore, the present invention is the above tumor-specific promoter for use in the gene therapy of cancer by the expression of a tumor-specific gene.

Furthermore, the present invention is the above tumor-specific promoter for use in the suicide gene therapy that has combined a vector in which a gene encoding a drug metabolizing enzyme has been ligated downstream of the tumor-specific promoter and a prodrug for cancer therapy that can be converted to an active form by said drug metabolizing enzyme.

Furthermore, the present invention is the above tumor-specific promoter for use in the gene therapy of cancer by any kinds of oncolytic viruses in which the expression of a virus gene has been altered using a tumor-specific promoter so that the virus can specifically propagate in tumor cells or tumor tissues.

BRIEF EXPLANATION OF THE DRAWINGS

FIG. 2A is a graph showing the result of measurement in which an in vitro sensitivity to gancyclovir was determined in normal human fibroblasts MRC-5 in which a gene containing a promoter obtained from the midkine gene has been linked with the TK gene and introduced, and the parent strain cell thereof.

FIG. 2B is a graph showing the result of measurement in which an in vitro sensitivity to gancyclovir was determined of immortalized human fibroblasts MRC-5 in which a gene containing a promoter obtained from the midkine gene has been linked with the TK gene and introduced, and the parent strain cell thereof.

FIG. 3A is a graph showing the result of measurement in which an in vitro sensitivity to gancyclovir was determined of lung cancer cells QG-56 in which a gene containing a promoter obtained from the midkine gene has been linked with the TK gene and introduced, and the parent strain cell thereof.

FIG. 3B is a graph showing the result of measurement in which an in vitro sensitivity to gancyclovir was determined of neuroblastoma NGP cells in which a gene containing a promoter obtained from the midkine gene has been linked with the TK gene and introduced, and the parent strain cell thereof.

FIG. 3C is a graph showing the result of measurement in which an in vitro sensitivity to gancyclovir was determined of normal fibroblasts HEF in which a gene containing a promoter obtained from the midkine gene has been linked with the TK gene and introduced, and the parent strain cell thereof.

FIG. 4A is a graph showing the result of measurement in which an in vivo sensitivity to gancyclovir was determined of lung cancer cells QG-56 in which a gene containing a promoter obtained from the midkine gene has been linked with the TK gene and introduced, and the parent strain cell thereof.

FIG. 4B is a graph showing the result of measurement in which an in vivo sensitivity to physiological saline administration was determined of lung cancer cells QG-56 in which a gene containing a promoter obtained from the midkine gene has been linked with the TK gene and introduced, and the parent strain cell thereof.

FIG. 5 is a graph showing the result of measurement in which the effect of the expression of the p53 tumor suppressor gene on the promoter activity of the 0.6 kb genomic fragment obtained from the midkine gene was examined.

BEST MODE FOR CARRYING OUT THE INVENTION

Figure 1:
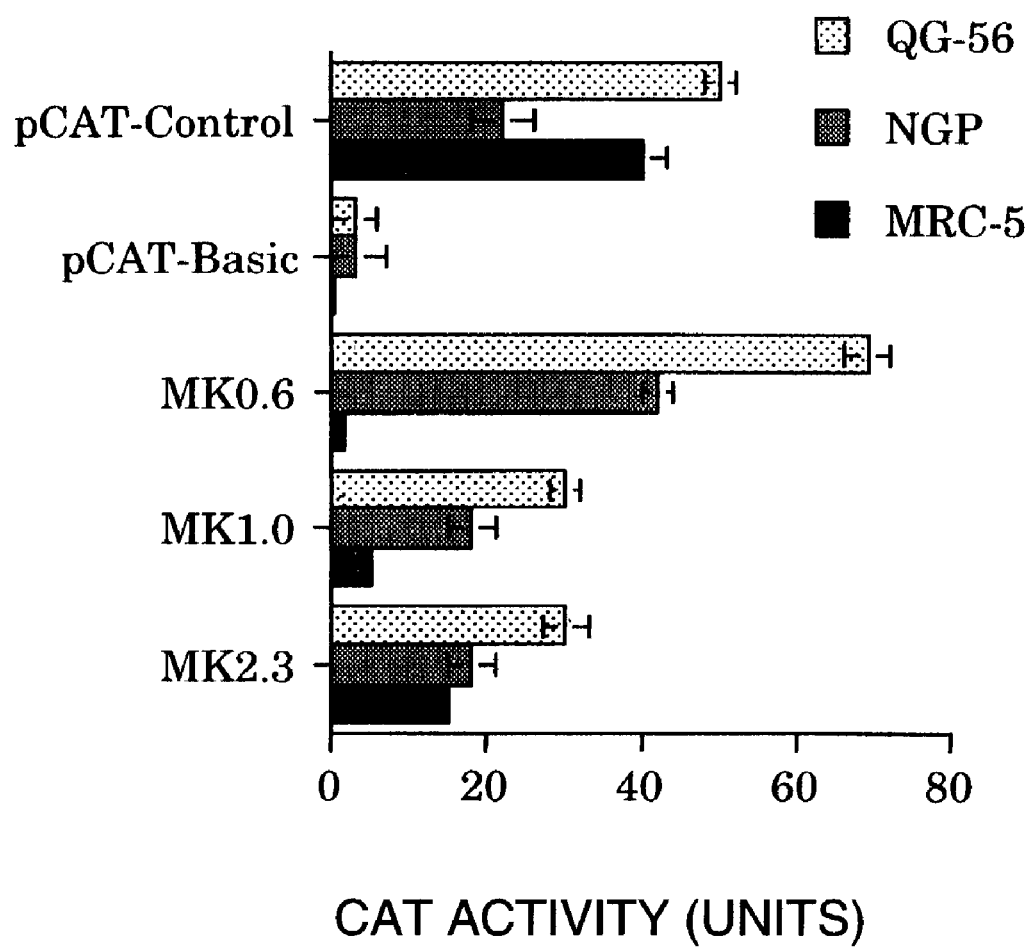
FIG. 1 is a graph showing the result of measurement in which the promoter activity of a promoter obtained from the midkine gene was determined based on a CAT assay.

The tumor-specific promoter of the present invention has sequences starting from any bases at positions 1–539 to a base at position 609 in the base sequence set forth in SEQ ID NO: 1 of the sequence listing, or sequences starting from any bases at positions 1–127 to a base at position 251 in the base sequence set forth in SEQ ID NO: 9. The invention also includes tumor-specific promoters that hybridizes to sequences from any bases at positions 1–539 to a base at position 609 in the base sequence set forth in SEQ ID NO: 1 of the sequence listing, or sequences from any bases at positions 1–127 to a base at position 251 in the base sequence set forth in SEQ ID NO: 9 at a stringent condition, and that have promoter functions similar to those base sequences.

The base sequence at positions 1–609 set forth in SEQ ID NO: 1 is a 609 bp base sequence from −559 to +50 when the first base sequence of exon 1 in the 5'-flanking sequence of the midkine gene was set as +1 (Uehara, K. et al., J Biochem., 111:563–567, 1992). The tumor-specific promoter of the present invention comprises sequences from any bases at positions 1–539 to a base at position 609 in the base sequence set forth in SEQ ID NO: 1. As shown in the Examples described below, it was elucidated that in order to function as a tumor-specific promoter contemplated in the present invention, the base sequence at least comprising bases 539–609 which are the 3'-end region of the base sequence set forth in SEQ ID NO: 1 is essential. Thus, the tumor-specific promoter of the present invention comprises base sequences from any bases at positions 1–539 to a base at position 609 in the base sequence set forth in SEQ ID NO: 1. As used herein, bases at positions 1, 539 and 609 in SEQ ID NO: 1 correspond to bases at positions −559, −21 and +50, respectively, when the first base sequence of exon 1 in the 5'-flanking region of the midkine gene is set as +1. As the base sequences from any bases at positions 1–539 to a base at position 609 in the base sequence set forth in SEQ ID NO: 1, base sequences at positions 1–609 (the base sequence of SEQ ID NO: 1), base sequences at positions 416–609 (the base sequence of SEQ ID NO: 5) or base sequences at positions 275–609 (the base sequence of SEQ ID NO: 4) are preferred.

Furthermore, those having base sequences from any bases at positions 1–127 to a base at position 251 in the base sequence set forth in SEQ ID NO: 9 are also tumor-specific promoters of the present invention. As shown in the Examples described below, it was elucidated that in order to function as a tumor-specific promoter contemplated in the present invention, the base sequences at least comprising bases 127–251 which are the 3'-end region of the base sequence set forth in SEQ ID NO: 9 is essential. The base sequence comprising bases 1–251 corresponds to base sequences at positions −213 to +38, and the base at position 127 of SEQ ID NO: 9 corresponds to position −87, when the base at position 1259 of the c-erbB-2 promoter gene (Accession No. J05264) registered at the NCB I GeneBank was set as the transcription initiation point +1.

In accordance with the present invention, those comprising base sequences that hybridize to any of the above base sequences under a stringent condition, and that has promoter functions similar to those base sequences are also tumor-specific promoters of the present invention. As used herein the base sequences that hybridizes under a stringent condition means base sequences that hybridizes to DNA having any of the above base sequences by Southern hybridization under the condition of reacting, for example, in a solution containing 6×SSC, 2×Denhardt's solution, 0.5% SDS and 0.1 mg/ml salmon sperm DNA at 65° C. for 12 hours. The tumor-specific promoters of the present invention are base sequences that hybridize under these conditions and that have promoter functions similar to the subject base sequences that hybridized, i.e. a similar degree of tumor-specificity and a similar degree of promoter activity. As such base sequences, there can be mentioned those having a homology of 65% or higher, preferably 75% or higher with the subject base sequence.

The above tumor-specific promoter of the present invention can be obtained based on the already reported sequence information of the midkine gene or the c-erbB-2 gene using a known method such as the PCR method. These methods can be readily carried out by a person skilled in the art according to a basic textbook such as Molecular Cloning 2nd Edt., Cold Spring Harbor Laboratory Press (1989). The above-mentioned tumor-specific promoter of the present invention having base sequences that hybridize under the above-mentioned stringent condition can be readily obtained by site-directed mutagenesis, a PCR method, or a common hybridization method and the like, and can specifically be carried out with reference to a basic textbook such as the above Molecular Cloning.

The tumor-specific promoter of the present invention having base sequences from any bases at positions 1–539 to a base at position 609 in the base sequence set forth in SEQ ID NO: 1 has, as is demonstrated in the Examples below, much higher tumor-specificity and a much higher promoter activity compared to a longer 2.3 kb and 1.0 kb promoter containing the base sequence of the promoter of the present invention at the 5'-end upstream region of the midkine gene. Furthermore, the tumor-specific promoter of the present invention has a characteristic feature that since it is under the influence of the p53 tumor suppressor gene, said p53 gene functioning normally in normal cells, the tumor-specific promoter of the present invention does not work, whereas the functions of the p53 gene disappears with the progress of tumorigenic transformation, and the tumor-specific promoter of the present invention works. The tumor-specific promoter of the present invention having a base sequence from any base at positions 1–127 to the base at position 251 in the above-mentioned base sequence set forth in SEQ ID NO: 9 also has much higher tumor-specificity, specifically for breast cancer, and a much higher promoter activity compared to a longer promoter region of the c-erbB-2 gene containing this base sequence.

The tumor-specific promoter of the present invention can be used in the gene therapy of cancer by the tumor-specific expression of genes, for example the suicide gene therapy that combines a gene encoding a drug metabolizing enzyme and a prodrug for cancer therapy, the immunological gene therapy that treats cancer by introducing cytokine genes etc. into tumor cells and thus by enhancing the immunological functions and the like.

As the suicide gene therapy, there can be mentioned cases in which the combination of a gene encoding a drug metabolizing enzyme and a prodrug for cancer therapy is the thymidine kinase gene of herpes simplex virus and gancyclovir or acyclovir, the cytosine deaminase gene and 5-fluorocytosine, the thymidine kinase gene of varicella-zoster virus and 6-methoxypurine arabinoside, the *E. coli* gpt gene and 6-thioxanthine, the cytochrome P450 2B1 gene and cyclophosphamide, the human deoxycytidine kinase gene and cytosine arabinoside, the *E. coli* UPRT gene and 5-fluorouracil, or the *E. coli* deoD gene and 6-methylpurine-2'-deoxyribonucleoside and the like. In order to actually perform the suicide gene therapy, an expression vector is constructed in which the tumor-specific promoter of the present invention and, down-stream thereof, a gene for a drug metabolizing enzyme have been integrated in a manner that permits the expression, the expression vector is introduced into tumor cells, and then a prodrug for gene therapy of cancer is administered so as to produce anti tumor effects. As the vectors, there can be mentioned vectors that are commonly used for gene introduction such as a retrovirus vector, an adenovirus vector, an adeno-associated virus vector and the like. Alternatively, a plasmid DNA in which the tumor-specific promoter of the present invention and, downstream thereof, a gene encoding a drug metabolizing enzyme have been integrated in a manner that permits the expression liposome, or is introduced into tumor cells with encapsulated liposome or polylysine-DNA-protein complexes. In order to introduce the genes, with these vectors, liposome encapsulated or the like may be injected intravenously or intraarterially or directly into the inside or the periphery of the tumors. At this time, the efficiency of gene introduction is possibly enhanced by the combination with electro-poration or ultrasonication. After the gene introduction, the prodrug for cancer therapy is administered in a common method such as oral, intravenous, and intraarterial administration.

The gene introduced is transcribed by the tumor-specific promoter of the present invention, and thereby the drug metabolizing enzyme is specifically expressed in the tumor cells and by the expressed drug metabolizing enzyme, the prodrug for cancer therapy is converted to an active therapeutic agent, and the converted therapeutic agent for cancer selectively kills cancer cells, and thus the suicide gene therapy is performed.

The procedure per se of such suicide gene therapy is already known, and the combination of the thymidine kinase gene of herpes simplex virus and gancyclovir has been clinically applied in brain tumor etc (Oldfield, E. H., Hum. Gene Ther., 4:39–69, 1993), and the combination of the cytosine deaminase gene and 5-fluorocytosine has also been suggested for potential clinical application in colon cancer etc. (Huber, B. E. et al., Cancer Res., 53:4619–4626, 1993), which methods are referrable when the gene therapy of the present invention is to be carried out.

As the immunological gene therapy using the tumor-specific promoter of the present invention, there can be used a method in which a gene encoding a cytokine such as interferons, TNF-α and interleukins is integrated in a method similar to the above suicide gene therapy into an expression vector together with the tumor-specific promoter of the present invention, or encapsulated into liposome, which is introduced into tumor cells to express the cytokine gene, thereby to enhance immune responses, a biological protection mechanism in human.

As the gene therapy by an oncolytic virus using the tumor-specific promoter of the present invention, there can be mentioned a method in which the tumor-specific promoter of the present invention is inserted upstream of E1A or E1B that is one of the early genes essential for the propagation of adenoviruses or is replaced with the E1A or E1B promoter, or the tumor-specific promoter of the present invention is inserted upstream of the corresponding early genes of herpes simplex virus or is replaced with the early gene promoters to construct an oncolytic virus that specifically propagates in tumor cells or tumor tissues thereby to kill tumor cells, and the virus is administered to treat cancer. For such gene therapy, reference is made to Heise, C. et al., J. Clin. Invest., 105:847–851, 2000, and other references.

Furthermore, it is possible, using the tumor-specific promoter of the present invention, to express an antisense gene of a oncogene or a tumor suppressor gene in unmutated form specifically in the tumors, and, as a result, it is possible to induce decarcinogenesis (normal return) of programmed cell death (apoptosis) and, furthermore, enhanced sensitivity of tumor cells to anti-cancer agents and enhanced sensitivity to radiation.

The gene therapy using the tumor-specific promoter of the present invention having base sequences from any bases at positions 1–539 to a base at position 609 in the base sequence set forth in SEQ ID NO: 1 is specifically effective for the treatment of cancer of the gastrointestinal tracts such as colon cancer, pancreatic cancer and hepatic cancer, lung cancer, breast cancer, neuroblastoma, brain tumors and the like. The gene therapy using the tumor-specific promoter of the present invention having base sequences from any bases at positions 1–127 to the base at position 251 in the above-mentioned base sequence set forth in SEQ ID NO: 9 is also effective for the treatment of breast cancer, esophageal cancer, gastric cancer, ovarian cancer etc., and specifically effective for the treatment of breast cancer.

The present invention will now be explained in more details with reference to Examples, but it should be noted that the present invention is not limited by these examples in any ways.

EXAMPLE 1

The Isolation of Tumor-specific Promoters from the Midkine Gene

A vector system for the analysis of the midkine transcription control region was obtained in the following manner.

A plasmid phgMK2.3K/CAT (Pedraza, CR et al., J. Biochem., 117:845–859, 1995) was cleaved with XhoI and NcoI or with XhoI and Eco47 III to obtain a 4.0 kb DNA fragment containing 1.0 kb of the midkine genomic gene and a 3.4 kb DNA fragment containing 0.6 kb of the midkine genomic gene, respectively. Using DNA ligase, these fragments were prepared as circular DNA. As a result, plasmids were obtained that contained respective 2.3 kb (MK2.3) of the human midkine genomic gene having the base sequence set forth in SEQ ID NO: 3, 1.0 kb (MK1.0) of the same gene having the base sequence. set forth in SEQ ID NO: 2, and 0.6 kb (MK0.6) of the same gene having the base sequence set forth in SEQ ID NO: 1 and, downstream thereof, the CAT (chloram-phenicol acetyltransferase) gene has been ligated.

EXAMPLE 2

Examination on Transcription Activity by Tumor-specific Promoters Derived From the Midkine Gene Using the above plasmid, or a plasmid pCAT-Control (manufactured by Promega) having the promoter of SV40 virus, and a plasmid pCAT-Basic (manufactured by Promega) containing no promoters, gene introduction was performed on the lung cancer cells QG-56, the neuroblastoma NGP, and the normal human fibroblasts MRC-5 that were being cultured in a DMEM (Sigma) supplemented with 10% bovine fetal serum. After 10 μg each of these plasmids and lipofectin (Life Technologies) were mixed, it was allowed to stand at room temperature for 30 minutes to form a complex. Then the complex, after removing the bovine fetal serum therefrom, was contacted with the cells. Eight hours later culture medium supplemented with bovine fetal serum was added, cultured for 40 hours, and then the gene-introduced cells were disrupted by ultrasonication. After centrifugation, the supernatants were used to examine their transcription activities with the known CAT assay method (Gorman, C M et al., Mol. Cell. Biol., 2:1044–1051, 1982) using [$^{14}$C]-chloramphenicol and acetyl CoA. At this time, in order to normalize the efficiency of gene introduction, 1 μg of the β-galactosidase gene (pCH110, manufactured by Amersham) was introduced at the same time, and the β-galactosidase activity (Heromel, P. et al., Cell, 39:653–662, 1984) was determined. The result obtained is shown in FIG. 1.

As can be seen from the result shown in FIG. 1, the transcription activity by the midkine genomic gene was as follows:

(a) When MK0.6 was used, the transcriptional activity was more potent in the tumor cells than MK1.0 or MK2.3 is activity, whereas it was rather decreased in the normal cells;

(b) When MK0.6 was used, the transcriptional activity was more potent than the promoter of SV40 virus in the tumor cells, whereas the promoter of SV40 virus was much more potent in the normal cells.

Thus, the present study revealed that the promoter activity by MK0.6 is specifically strong in tumors, whereas the tumor-specificity of a promoter activity by MK2.3 or MK1.0 is weak.

EXAMPLE 3

Tumor-specific Cytotoxic Effects Using Tumor-specific Promoters Derived From the Midkine Gene (1) In order to examine cytotoxic effects by the transcription activity of the promoter obtained from the midkine gene, herpes simplex virus thymidine kinase (HSV-TK), a suicide gene, was ligated downstream of MK0.6 and MK2.3, and the plasmid was introduced in cells, and a prodrug gancyclovir (GCV) was added into the culture medium of the gene-introduced cells. The method of determining the cytotoxic effect by this system is as described in Moolten, FL. Cancer Gene Ther., 1:279–287, 1994.

First, the CMV promoter of pcDNA3 (manufactured by Invitrogen) was removed using NruI and HindIII sites, to which MK2.3 or Mk0.6 was inserted, and then using the EcoRV site, the HSV-TK gene excised from pMK (Brinster, R L et al., Cell, 27:223–231, 1981) with BglI and EcoRI was inserted. Each of the plasmids thus obtained (MK2.3-TK and MK0.6-TK) was introduced, as described above, using lipofectin into MRC-5 which are normal cells, or MRC-5 cells that had been immortalized by inactivating the functions of the p53 tumor suppressor gene. In order to utilize the expression of the Neo gene contained in pcDNA3 as drug resistant markers, the cells were cultured with 400 μg/ml of G418 (manufactured by Life Technologies) for ten days to establish the cells that expressed MK2.3-TK and MK0.6-TK, respectively. These cells were then plated at 500 cells/well of 96-well culture plates, and were cultured in the presence of various concentrations of GCV (manufactured by F. Hoffman-La Roche) for seven days. The survival rate of the cells was examined using the Cell Counting Kit-8 (manufactured by Dojin Kagaku). The survival of the cells at a GCV concentration of 0 μg/ml was set as 100%, and the survival for each experiment group is shown in terms of percentage in FIG. 2A and FIG. 2B.

As can be seen from the result shown in FIG. 2A, in the case of normal MRC-5 cells, when the transcription of the HSV-TK gene was controlled by the MK2.3 promoter, their sensitivity to GCV was 500-fold higher compared to that of the parent strain, and the cells died at lower concentrations of GCV, whereas when the transcription of the HSV-TK gene was controlled by the MK0.6 promoter, their sensitivity to GCV was identical with that of the parent strain.

As can be seen from the result shown in FIG. 2B, when immortalized MRC-5 cells was transfected with the HSV-TK gene powered by both MK2.3 and MK0.6 promoters, their sensitivity to GCV increased by 1000-fold compared to that of the parent strain.

Thus, when the MK2.3 promoter was used to control the expression of HSV-TK gene, cytotoxic effects were produced in the immortalized cells and the normal cells, whereas when the MK0.6 promoter was used, the cytotoxic effects were only produced in the immortalized cells, and no cytotoxic effects were achieved in the normal cells. These data indicate that the MK0.6 promoter acts as much more tumor-specific than the MK2.3 promoter as is also seen in the result of FIG. 1.

(2) Then, the tumor-specificity of this MK0.6 promoter was examined using the human tumor cells and normal fibroblasts. As described above, MK0.6-TK was introduced into various types of cells using lipofectin, and they were cultured in the presence of 400 μg/ml of G418 for ten days to obtain cells in which the MK0.6-TK gene was expressed. Thus, these gene-introduced cells were plated at 500 cells/well of 96-well culture plates, and were cultured in the presence of various concentrations of GCV for seven days. The survival rate of the cells was examined using the Cell Counting Kit-8. The results obtained are shown in FIG. 3A, FIG. 3B and FIG. 3C.

As can be seen from the results shown in FIG. 3A and FIG. 3B, in tumor cells, QG-56 and NGP, the sensitivity to GCV increased by 1000-fold compared their respective parent strain. In contrast, as can be seen from the result shown in FIG. 3C, the sensitivity of normal fibroblasts HEF to GCV remained the same as that of compared the parent strain. Thus, these data revealed that the MK0.6 promoter enabled, tumor-specific gene expression, and the linked suicide gene HSV-TK produced tumor-specific cytotoxic effects with GCV. Furthermore, the maximum blood concentration of GCV which is currently used for the treatment of cytomegalovirus infections is 1 μg/ml, and therefore the concentration of 0.1 μg/ml at which the cytotoxic effects by GCV was obtained as shown in this experiment is below this level, suggesting that TK expression controlled by MK0.6 produces highly safe and effective therapeutic effects.

EXAMPLE 4

In Vivo Anti-tumor Effects Using the Tumor-specific Promoter Derived from the Midkine Gene As described above, using lipofectin, MK0.6-TK gene was introduced into QG-56 cells, and they were cultured in the presence of 400 µg/ml of G418 for ten days to obtain QG-56 cells in which the MK0.6-TK genes was expressed. These gene-introduced cells and the parent strain cells were subcutaneously inoculated into 6-week old female BALB/c nude mice (provided by Nippon SLC) at $1 \times 10^6$ cells to develop subcutaneous tumors. When the tumor volume reached to 100 mm$^3$, 30 mg/kg of GCV or the same amount of physiological saline was intraperitoneally administered for five days. Changes in tumor volume after the inoculation of QG-56 cells were measured, and the results obtained are shown in FIG. 4A and FIG. 4B.

As can be seen from the result shown in FIG. 4A, all the seven QG-56 tumors in which the MK0.6-TK was transfected disappeared and did not relapse, after GCV administration, whereas the parent strain tumor had no regression and the growth of the tumor continued even in the presence of GCV. As can be seen from the result shown in FIG. 4B, in the physiological saline administration group, there were no changes in the growth rate of both tumors, the MK0.6-TK gene-expressed tumor and the parent strain tumor. Thus, these data revealed that the MK0.6-TK promoter activates the transcription of the HSV-TK gene and the transcription activity permits the complete disappearance of transfected tumors by GCV administration.

EXAMPLE 5

The Biological Characteristics of the Midkine Promoter

In at least about 50% of human solid tumors, the loss of p53 gene functions is observed, and forced expression of-the wild-type p53 gene in tumors arrests tumor growth in some cases. Thus, using the MRC-5 cells that had been immortalized by destroying the functions of the p53 gene, DNA plasmid was introduced in which the luciferase gene, a reporter gene, was ligated downstream of the MK0.6 promoter, and the transcription activity of the MK0.6 promoter under the expression of the wild-type p53 gene was examined.

For this purpose, the MK0.6-CAT plasmid prepared in Example 1 was cleaved with HindIII, and the MK0.6 kb gene obtained was inserted into the HindIII site of pGL2-Basic (manufactured by Promega). Furthermore, a plasmid (Baker, S J et al., Science, 249:912–915, 1990) (CMV-p53) in which the wild-type p53 gene was ligated downstream of the cytomegalovirus promoter, and a control plasmid (CMV-p53R) in which this plasmid was cleaved with BamHI and the insert p53cDNA was ligated in the opposite direction of the CMV promoter were constructed and used. Thus, the immortalized MRC-5 cells that had been cultured in a 10 cm petri dish, were transfected with MK0.6-luciferase (3 µg) and each amount of CMV-p53 plasmid (0–1 µg), or MK0.6-luciferase (3 µg) and each amount of CMV-p53R plasmid (0–1 µg) using lipofectin as described above. After 48 hours-culture, the cells were disrupted using the Dual-Luciferase Reporter Assay System (manufactured by Promega), and the Firefly luciferase activity therein was determined using the reagents in the same kit. In order to normalize the efficiency of transfection, 1 µg of pRL-TK plasmid (manufactured by Promega) was included in each transfection, and the Renilla luciferase activity by the TK promoter was determined, based on which the Firefly luciferase activity was corrected. The result obtained is shown in FIG. 5.

As can be seen from the result in FIG. 5, with the increase in the amounts of the CMV-p53 plasmid introduced, the MK0.6 promoter activity decreased, whereas there were no changes in the MK0.6 promoter activity in the cotrol CMV-p53R plasmid introduced group. Thus, the data revealed that the MK0.6 promoter is under the influence of the p53 tumor suppressor gene. Since the functions of the p53 gene is intact in the normal cells and tumorigenesis is associated with the loss of functions of the gene, the MK0.6 promoter does not work in normal but works in transformed cells.

EXAMPLE 6

Identification of the Minimum Midkine Promoter Region 1

As can be seen from the above Examples, it was revealed that in the promoter region of the human midkine genomic gene, specifically in 609 bp fragment from –559 to +50 (the first base sequence of exon 1 is defined as +1), there is a tumor-specific promoter region. In order to further narrow down this region, vector DNA for analysis of the midkine transcription control region was obtained in the following manner.

Using the PCR method based on the information of the midkine genomic DNA, a DNA fragment that corresponds to a 335 bp region (MK335bp) from –285 to +50 and that has the base sequence set forth in SEQ ID NO: 4 was synthesized, and after confirming the sequences, it was inserted into pCR2.1 (manufactured by Invitrogen). After excising MK335bp from this DNA, it was ligated to pGL2-Basic (manufactured by Promega) to construct a plasmid for detecting promoter activity. Furthermore, using pGL2-Control (manufactured by Promega) containing the promoter of SV40 virus and pGL2-Basic containing a similarly constructed 609 bp midkine promoter (MK0.6), promoter activity was examined by the following method.

The lung cancer cells QG-56, PC-1, and human breast cancer cells BT549 that were cultured in DMEM (Sigma) supplemented with 10% bovine fetal serum, were transfected. After 10 µg each of these plasmids and lipofectin (manufactured by Life Technologies) were mixed, it was allowed to stand at room temperature for 30 minutes to form a complex. Then the complex, after removing the bovine fetal serum therefrom, was contacted with the cells. Eight hours later culture medium supplemented with bovine fetal serum was added. After 48 hours-culture, the gene-introduced cells were disrupted using the Dual-Luciferase Reporter Assay System (manufactured by Promega), and the Firefly luciferase activity therein was determiened using the reagents in the same kit. In order to normalize the efficiency of gene introduction, 1 µg of pRL-TK plasmid (manufactured by Promega) was included in each gene introduction group, and the Renilla luciferase activity by the TK promoter was determined, based on which the Firefly luciferase activity was corrected.

Figure 6:
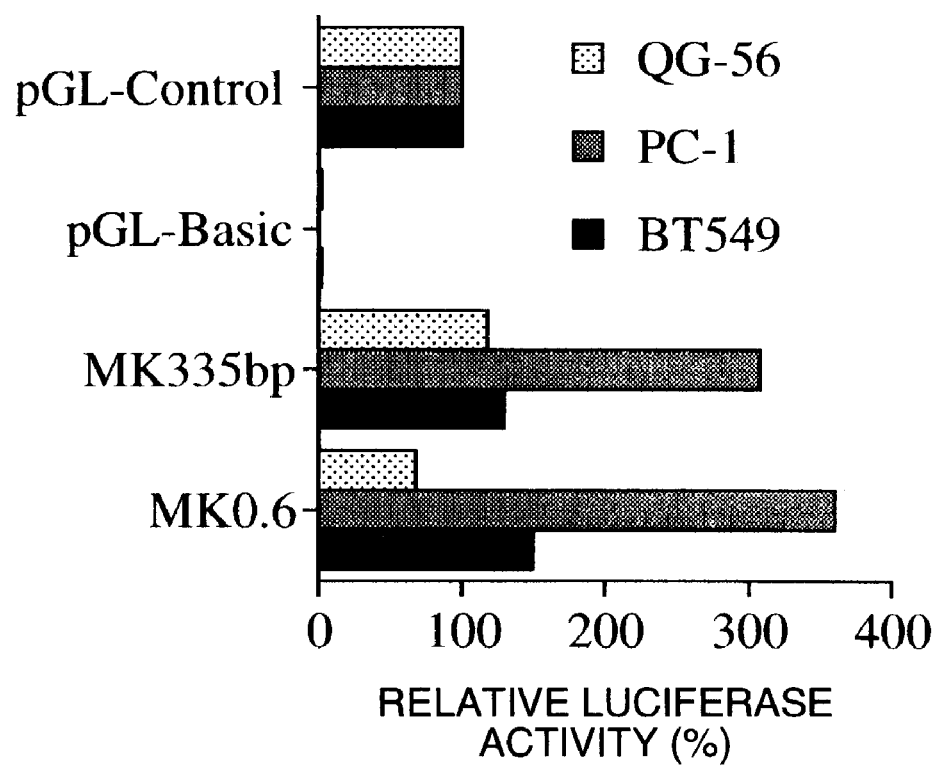
FIG. 6 is a graph showing the result of measurement in which the promoter activity of a promoter obtained from the midkine gene was determined based on a luciferase assay wherein the promoter activity of the SV40 promoter (by pGL-Control) was set as 100%.

The result obtained is shown in FIG. 6. As a result, it was revealed that the promoter activity of MK335bp, though differs with the tumor cells, had almost the same activity as that of MK0.6 in tumor cells.

EXAMPLE 7

Identification of the Minimum Midkine Promoter Region 2

The MK335bp fragment excised from the above pCR2.1 with EcoRI digestion was inserted into the EcoRI site of pcDNA3 (manufactured by Invitrogen) which was digested with NruI and HindIII to remove promoter of cytomegalovirus. Using the HindIII site contained in the primers for PCR and the XbaI site of pcDNA3, the above DNA was cleaved. The β-galactosidase gene excised from pCH110 (manufactured by Pharmacia) with HindIII and BamHI digestion was ligated at blunt ends of the above digested DNA. Then, after digesting this DNA with KpnI and BamHI, it was sequentially digested with Exonuclease III. After the lengths of these DNA were confirmed by agarose gel electrophoresis, they were prepared to form circular DNA with DNA ligase. Then, the base sequence of the midkine genomic region was determined, and two DNA fragments were obtained that contained the β-galactosidase gene downstream of either DNA that has a region (MK194bp) from −144 to +50 and has the base sequence set forth in SEQ ID NO: 5, or DNA that has a region (MK70bp) from −20 to +50 and has the base sequence set forth in SEQ ID NO: 6.

Using lipofectin, these DNA were introduced into the immortalized human fibroblasts MRC-5 that were being cultured in DMEM (Sigma) supplemented with 10% bovine fetal serum. After 48 hours, they were then cultured in the presence of 400 μg/ml of G418 for ten days to obtain the gene-introduced MRC-5 cells. These cells were stained according to a known method (Topf, N. et al., Gene Ther., 5:507–513, 1998) that developes a blue color when the β-galactosidase gene is expressed. The result is shown in Table 1.

TABLE 1

| DNA introduced | Staining ratio of immortalized MRC-5 cells |
| --- | --- |
| MK335 bp/β-galactosidase gene | 100% |
| MK194 bp/β-galactosidase gene | 100% |
| MK70 bp/β-galactosidase gene | 0% |

As shown in Table 1, when DNA harboring MK335bp and MK194bp as the promoter was introduced, MRC-5 cells were stained blue, whereas when DNA harboring MK70bp as the promoter was introduced, MRC-5 cells were not stained at all. Thus, the data revealed that the minimum midkine promoter the data region is localized in 194 bp fragment from −144 to +50, to be more precisely in a fragment longer than the that from −20 to +50.

EXAMPLE 8

Examination of Transcription Activity by the c-erbB-2 Promoter

Figure 7A:
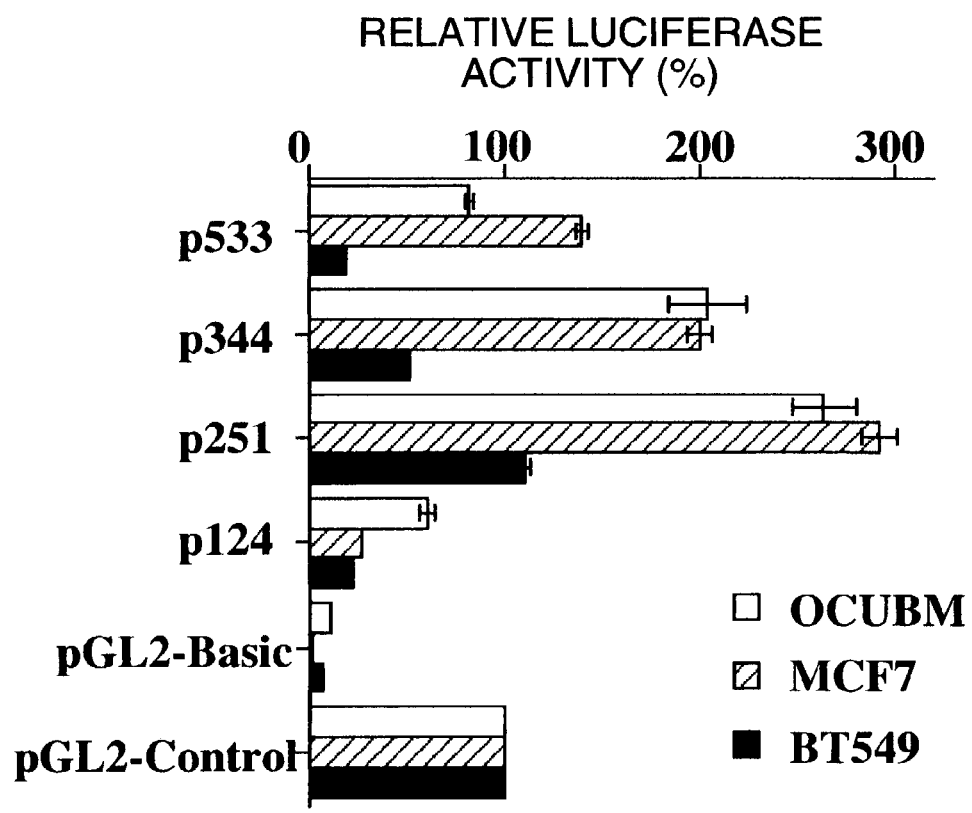
FIG. 7A is a graph showing the result of measurement in which the promoter activity of a promoter obtained from the human c-erbB-2 gene was determined based on a luciferase assay. The cells used were all human breast cancer cells and the promoter activity of the SV40 promoter (by pGL2-Control) was set as 100%.

With the transcription initiation site of the c-erbB-2 gene as +1, DNA that corresponded to a genomic region (p533) from −435 to +38 and that had the sequence set forth in SEQ ID NO: 7 was amplified by the PCR method, and then the DNA fragment was integrated into the pGEM-TEasy (manufactured by Promega), and the sequences of the PCR product was determined. Thus, after inserting this PCR product into the SmaI site of pGL2-Basic (manufactured by Promega), it was cleaved with BlnI/SmaI, PstI/SmaI, and BssHII/SmaI using the restriction enzyme sites present on the c-erbB-2 genomic gene to construct plasmids in which the genomic regions of c-erbB-2, p344 (−306/+38) (DNA having the base sequence set forth in SEQ ID NO: 8), p251 (−213/+38) (DNA having the base sequence set forth in SEQ ID NO: 9) and p124 (−86/+38) (DNA having the base sequence set forth in SEQ ID NO: 10) are localized upstream of the Firefly luciferase gene, respectively. Using the plasmid pGL2-Control (manufactured by Promega) having the promoter of SV40 virus and the plasmid pGL2-Basic (manufactured by Promega) containing no promoters, gene introduction was performed in human breast cancer cells OCUBM, MCF7, BT549, normal human fibroblasts HEF, MRC-5, human malignant melanoma A875, and human lung cancer cells QG-56, all of which were cultured in DMEM (Sigma) supplemented with 10% bovine fetal serum. Firstly, after 10 μg each of these plasmids and lipofectin (Life Technologies) were mixed, it was allowed to stand at room temperature for 30 minutes to form a complex of DNA and lipid. Then the complex, after removing the bovine fetal serum therefrom, was contacted with the cells. Eight hours later culture medium supplemented with bovine fetal serum was added. After 48 hours-culture, the cells were disrupted using the Dual-Luciferase Reporter Assay System (manufactured by Promega), and the Firefly luciferase activity therein was determined using the reagents in the same kit. In order to normalize the efficiency of gene introduction, 1 μg of pRL-TK plasmid (manufactured by Promega) was included in each gene-introduced group, and the Renilla luciferase activity by the TK promoter was determined, based on which the Firefly luciferase activity was corrected. The results obtained are shown in FIGS. 7A to C.

As can be seen from these results, the properties of c-erbB-2 promoter were as follows:

(a) In human breast cancer cells, the p251 promoter had a higher transcription activity than the p533 promoter which is conventionally used in the current gene therapy protocol, and the p251 promoter activity was more potent than the promoter of SV40 virus. On the other hand, the transcription activity of the p124 promoter in which the 5' region was further deleted marked low compared with the p251 promoter (FIG. 7A). This revealed that in order to possess the promoter function properly, it is necessary to have sequences at least longer than the p124 promoter has.

Figure 7B:
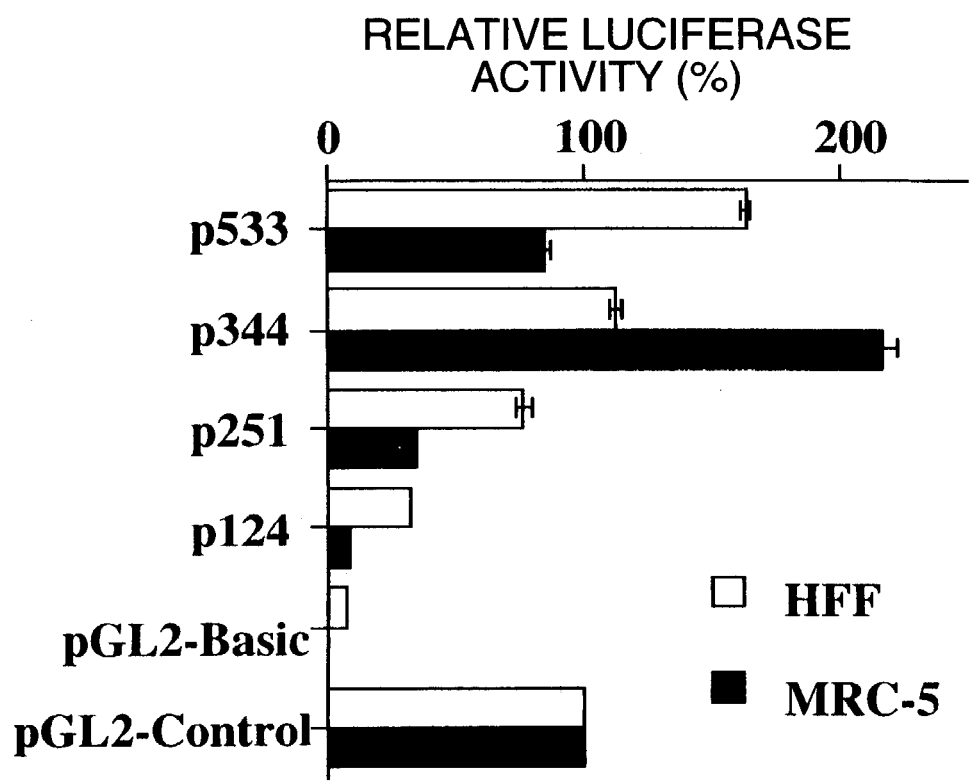
FIG. 7B is a graph showing the result of measurement in which the promoter activity of a promoter obtained from the human c-erbB-2 gene was determined based on a luciferase assay. The cells used were all human normal fibroblasts and the promoter activity of the SV40 promoter (pGL2-Control) was set as 100%.
Figure 7C:
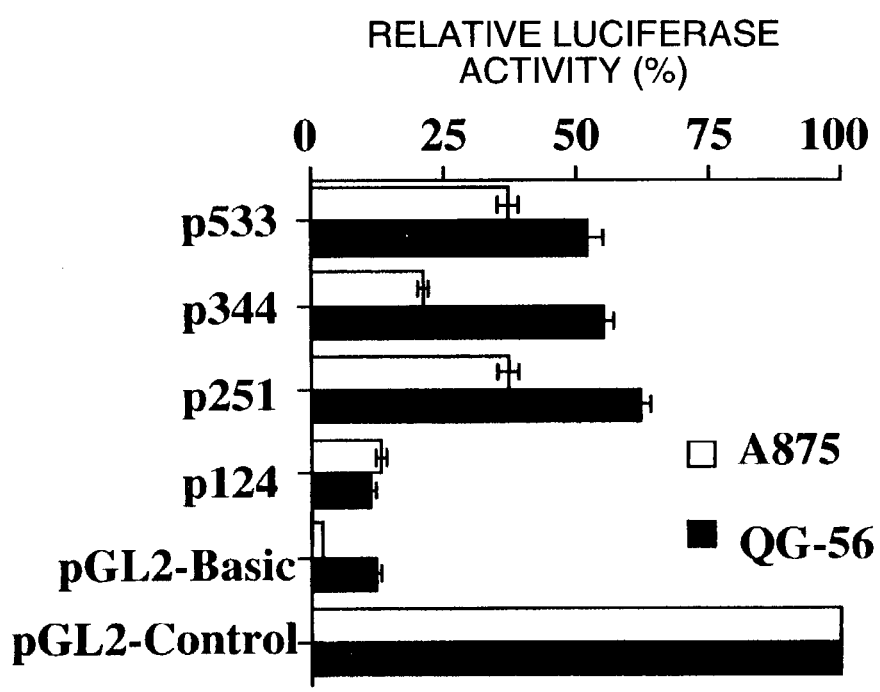
FIG. 7C is a graph showing the result of measurement in which the promoter activity of a promoter obtained from the human c-erbB-2 gene was determined based on a luciferase activity. The cells used were human malignant melanoma cells and human lung cancer cells and the promoter activity of the SV40 promoter (pGL2-Control) was set as 100%.

(b) In human fibroblasts, the p533 and p344 promoter activities were more potent than the SV40 promoter activity in some cases, but the transcription activity of the p251 promoter remained low compared with the p344 promoter and with the p533 promoter and lower than the SV40 promoter (FIG. 7B).

(c) In the case of the human malignant melanoma cells and the human lung cancer cells, all of the promoters including p517, p344, p251 and p124 showed transcription activity lower than the SV40 promoter. The transcription activity of the p251 promoter is about the same as that of p533 promoter (FIG. 7C). Thus, the data revealed that the promoter activity of p251 has a higher transcription activity in breast cancer cells compared with the p533 promoter and the p251 promoter is more useful than the conventional p533 promoter based on the comparison with the data using normal cells.

EXAMPLE 9

Breast Cancer-specific Cytotoxic Effects Using the c-erbB-2 Promoter

Figure 8A:
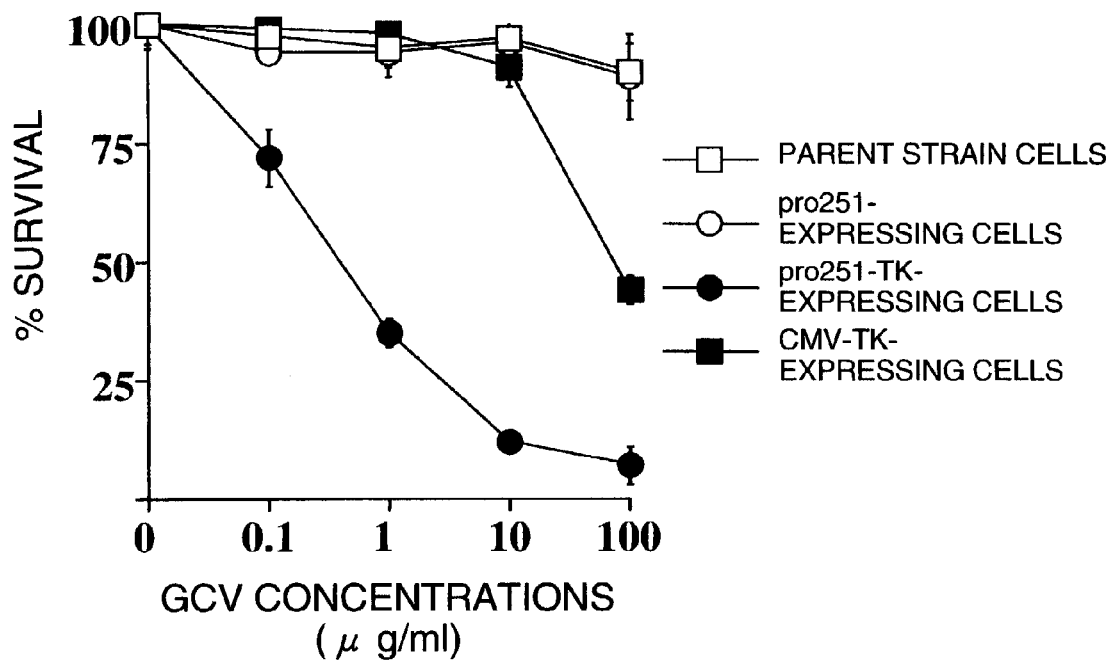
FIG. 8A is a graph showing the result of measurement in which an in vitro sensitivity to gancyclovir was determined of human breast cancer cells MCF7 in which a gene containing a promoter obtained from the human c-erbB-2 gene or the cytomegalovirus promoter has been linked with or without the TK gene and introduced, and the parent strain cell thereof. The survival rate at a gancyclovir concentration of 0 was set as 100%.
Figure 8B:
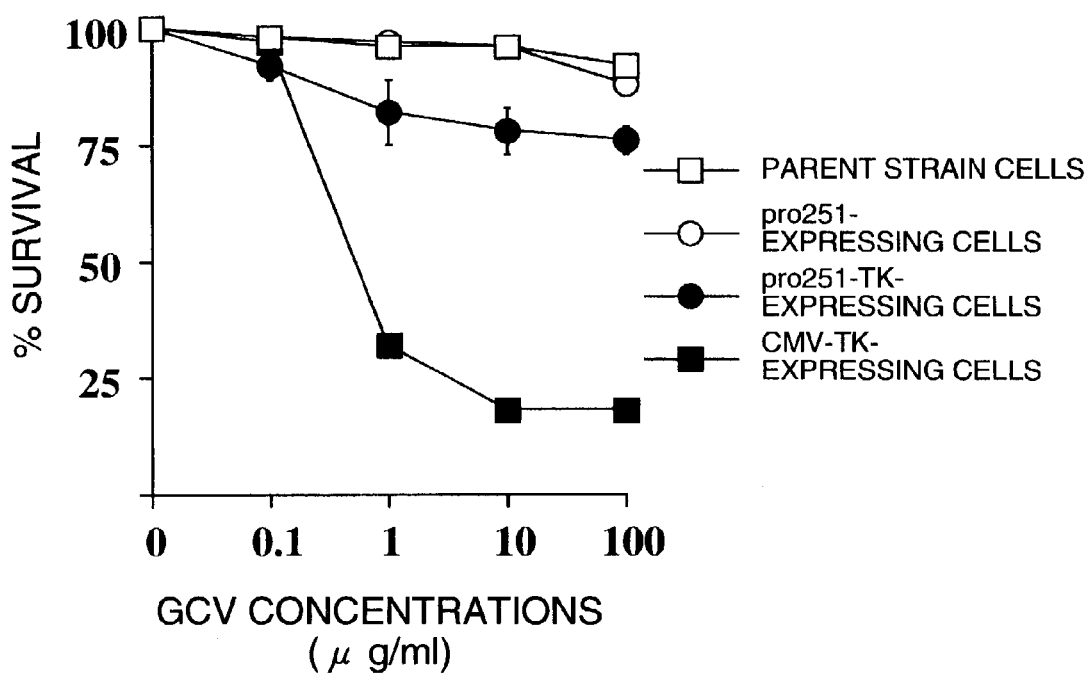
FIG. 8B is a graph showing the result of measurement in which an in vitro sensitivity to gancyclovir was determined of a human malignant melanoma A875 in which a gene containing a promoter obtained from the human c-erbB-2 gene or the cytomegalovirus promoter has been linked with or without TK gene and introduced, and the parent strain cell thereof. The survival rate at a gancyclovir concentration of 0 was set as 100%.

In order to examine the cytotoxic effects using the p251 promoter, a suicide gene HSV-TK was ligated downstream of this promoter region (pro251-TK), this plasmid was expressed in cells, and a prodrug GCV was added to the culture of the gene-introduced cells. The measurement of cytotoxic effects by this system was carried out according to the method described in Moolten, Fla. Cancer Gene Ther., 1:279–287, 1994. Firstly, the cytomegalovirus (CMV) promoter of pcDNA3 (manufactured by Invitrogen) was removed using NruI and HindIII sites, into which the p251 promoter was inserted and then using the EcoRV site, the HSV-TK gene excised from pMK (Brinster, R L et al., Cell, 27:223–231, 1981) with BglI and EcoRI was inserted (pro251-TK). As a control, a pcDN3-derived plasmid (pro251) that contains no HSV-TK gene but has integrated the p251 promoter, and a pcDNA3-derived plasmid (CMV-TK) that has the HSV-TK gene and permits the expression of the HSV-TK gene were also used. Each of the plasmids (pro221, pro251-TK, CMV-TK) was introduced using lipofectin into the breast cancer cells MCF7 or non-breast cancer cells A875. In order to utilize the expression of the Neo gene contained in pcDNA3 as a drug resistant marker, the transfected cells were cultured with 400 μg/ml of G418 (manufactured by Life Technologies) for ten days to establish the cells that express a respective gene. Then, these cells were plated at 500 cells/well of 96-well culture plates, and were cultured in the presence of various concentrations of GCV (manufactured by F. Hoffman-La Roche) for seven days. The survival rate of the cells was examined using the Cell Counting Kit-8 (manufactured by Dojin Kagaku). The survival of the cells at a GCV concentration of 0 μg/ml was set as 100%, and the survival for each experiment group was shown in terms of percentage (FIG. 8A and B). The result revealed the followings:
(a) When the HSV-TK gene was expressed under the p251 promoter, the MCF7 cells showed greater sensitivity to GCV than the parent strain and transfected cells with the HSV-TK gene was expressed under the CMV promoter (FIG. 8A).
(b) When the CMV promoter was used, the transfected A875 cells were more sensitive to GCV compared with parent strain, but when the p251 promoter was used, the GCV sensitivity of the transfected A875 cells was very weak compared with of the parent strain (FIG. 8B). Thus, when the p251 promoter was used in the breast cancer cells, cytotoxic effects produced were greater than those by the CMV promoter, whereas the effects by the p251 promoter was very low in the non-breast cancer cells.

EXAMPLE 10

The in Vivo Anti-cancer Effects Using the c-erbB-2 Promoter

Figure 9:
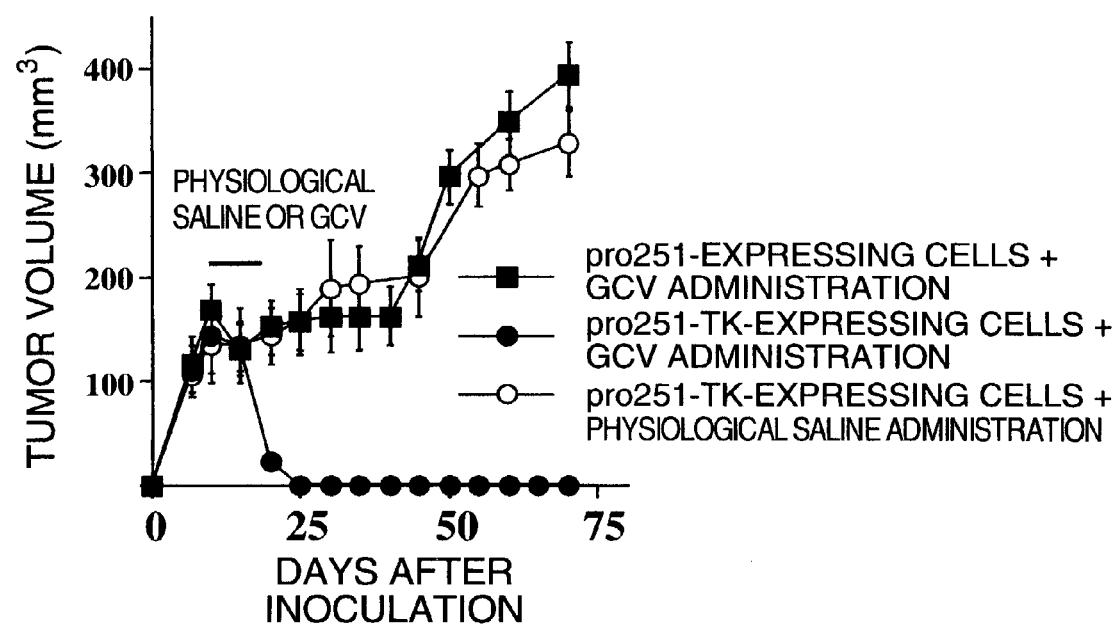
FIG. 9 is a graph showing the result of measurement in which an in vivo sensitivity to gancyclovir or physiological saline was determined of human breast cancer cells MCF7 in which a gene containing a promoter obtained from the human c-erbB-2 gene has been introduced and the parent stain cell thereof.

In a similar manner to the above Examples, the gene-introduced MCF7 cells in which pro251 or pro251-TK were transfected were inoculated into BALB/c nude mice at $1 \times 10^6$ cells to form subcutaneous tumors. When the tumor volume reached to 150 mm$^3$, 30 mg/kg of GCV or the same amount of physiological saline was intraperitoneally administered for five consecutive days. The results revealed the followings:
(a) Among the GCV administered group, all of the seven tumors in which the pro251-TK gene was expressed disappeared and the mice did not relapse thereafter, whereas the pro251-expressing tumors used as the control, did not regress and the growth of the tumors continued (FIG. 9).
(b) The growth rate of the tumor in which the pro251-TK gene was expressed and received physiological saline was identical with that of the pro251-expressing tumors that were treated with GCV administration. Thus, the data revealed that the p251 promoter mediated the transcription activation of the HSV-TK gene and had a transcription activity that permitted complete disappearance of tumors by GCV administration.

INDUSTRIAL APPLICABILITY

As hereinabove described in detail, the tumor-specific promoter of the present invention that has a 609-bp fragment obtained from the 5' upstream region of the midkine gene or a 251 bp fragment in the promoter region in the c-erbB-2 gene have high tumor-specificity and great promoter activity. Thus, by using the tumor-specific promoter of the present invention, very safe and effective gene therapy can be attained.

---

The invention claimed is:

1. A tumor-specific promoter that consists of a nucleotide sequence starting from any base at positions 1–539 to the base at position 609 in the nucleotide sequence set forth in SEQ ID NO: 1.

2. A tumor-specific promoter consisting of a nucleotide sequence selected from the group consisting of SEQ ID NO: 1, SEQ ID NO: 5 and SEQ ID NO: 4.

3. A tumor-specific promoter of at least 71 bp to about 0.6 kb in length, wherein said tumor-specific promoter comprises a nucleotide sequence starting from any base at positions 1–539 to the base at position 609 of SEQ ID NO: 1.

4. A method of treating a tumor in a subject wherein said tumor is caused by p53 inactivation, comprising administering a vector directly into said tumor, wherein said vector comprises the tumor-specific promoter according to any one of claims 1, 2 or 3, said promoter is operably linked to a nucleotide sequence coding for a drug metabolizing enzyme, and additionally administering a prodrug directly into said tumor, wherein said enzyme converts said prodrug to an active form in said subject.

5. The method according to claim 4, wherein said nucleotide sequence coding for said enzyme and said prodrug, in combinations are selected from the group consisting of the thymidine kinase gene of herpes simplex virus and gancyclovir or acyclovir, the cytosine deaminase gene and 5-fluorocytosine, the thymidine kinase gene of varicella-zoster virus and 6-methoxypurine arabinoside, the E. coli gpt gene and 6-thioxanthine, the cytochrome P450 2B1 gene and cyclophosphamide, the human deoxycytidine kinase gene and cytosine arabinoside, the E. coli UPRT gene and 5-fluorouracil, and the E. coli deoD gene and 6-methylpurine-2'-deoxyribonucleoside.

6. The method according to claim 4, wherein said tumor is selected from the group consisting of breast tumor, ovarian tumor, gastric tumor or esophageal tumor.

7. A method of treating a tumor in a subject wherein said tumor is caused by p53 inactivation, comprising administering an oncolytic virus directly into said tumor, wherein said virus comprises the tumor-specific promoter according to any one of claims 1, 2 or 3, and a gene of said oncolytic virus necessary for viral propagation is operably linked to said promoter so that said virus propagates specifically in said tumor.

8. The method according to claim 7, wherein said tumor is selected from the group consisting of breast tumor, ovarian tumor, gastric tumor or esophageal tumor.

9. A vector comprising the tumor-specific promoter according to any one of claims 1, 2 or 3, wherein said tumor-specific promoter is operably linked to a nucleotide sequence coding for a drug metabolizing enzyme, wherein said drug metabolizing enzyme converts a prodrug to an active form.

10. The vector according to claim 9, wherein said nucleotide sequence coding for the enzyme and said prodrug, in combination, are selected from the group consisting of the thymidine kinase gene of herpes simplex virus and gancyclovir or acyclovir, the cytosine deaminase gene and 5-fluorocytosine, the thymidine kinase gene of varicella-zoster virus and 6-methoxypurine arabinoside, the E. coli gpt gene and 6-thioxanthine, the cytochrome P450 2B1 gene and cyclophosphamide, the human deoxycytidine kinase gene and cytosine arabinoside, the E. coli UPRT gene and 5-fluorouracil, and the E. coli deoD gene and 6-methylpurine-2'-deoxyribonucleoside.

11. An oncolytic virus vector comprising the tumor-specific promoter according to any one of claims 1, 2, or 3, wherein said tumor-specific promoter is operably linked to a gene necessary for the propagation of the virus.

* * * * *